(12) United States Patent
Higashi et al.

(10) Patent No.: US 9,046,549 B2
(45) Date of Patent: Jun. 2, 2015

(54) METHOD FOR MANUFACTURING PRESSURE SENSING DEVICE

(71) Applicants: Yoshihiro Higashi, Kanagawa-ken (JP); Michiko Hara, Kanagawa-ken (JP); Hideaki Fukuzawa, Kanagawa-ken (JP); Yoshihiko Fuji, Kanagawa-ken (JP); Hiromi Yuasa, Kanagawa-ken (JP); Tomohiko Nagata, Kanagawa-ken (JP)

(72) Inventors: Yoshihiro Higashi, Kanagawa-ken (JP); Michiko Hara, Kanagawa-ken (JP); Hideaki Fukuzawa, Kanagawa-ken (JP); Yoshihiko Fuji, Kanagawa-ken (JP); Hiromi Yuasa, Kanagawa-ken (JP); Tomohiko Nagata, Kanagawa-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 310 days.

(21) Appl. No.: 13/710,718

(22) Filed: Dec. 11, 2012

(65) Prior Publication Data
US 2013/0255069 A1    Oct. 3, 2013

(30) Foreign Application Priority Data
Mar. 28, 2012    (JP) .................................. 2012-075148

(51) Int. Cl.
*G01R 3/00* (2006.01)
*G01L 9/16* (2006.01)
*G01L 1/12* (2006.01)
*G01L 9/00* (2006.01)
*A61B 5/021* (2006.01)

(52) U.S. Cl.
CPC .............. *G01R 3/00* (2013.01); *Y10T 29/49007* (2015.01); *G01L 9/16* (2013.01); *G01L 1/125* (2013.01); *G01L 9/0048* (2013.01); *A61B 5/02141* (2013.01); *A61B 2562/0247* (2013.01)

(58) Field of Classification Search
CPC ..................... Y10T 29/49007; A61B 5/02141; A61B 5/021
USPC .................... 29/595, 830, 831, 832, 834, 843
See application file for complete search history.

(56) References Cited

U.S. PATENT DOCUMENTS 4,922,606 A * 5/1990 Alexander et al. .............. 29/839
6,621,266 B1 * 9/2003 Payne et al. ................... 324/260
(Continued)

FOREIGN PATENT DOCUMENTS

JP    2002-148132    5/2002

OTHER PUBLICATIONS

U.S. Appl. No. 14/045,153, filed Oct. 3, 2013, Higashi, et al.
(Continued)

*Primary Examiner* — Peter DungBa Vo
*Assistant Examiner* — Kaying Kue
(74) *Attorney, Agent, or Firm* — Oblon, McClelland, Maier & Neustadt, L.L.P.

(57) ABSTRACT

According to one embodiment, a method for manufacturing a pressure sensing device includes preparing a sensor unit and a mounting substrate. The sensor unit includes: a membrane body; and an element unit provided on the membrane body. The element unit includes: a first electrode; a second electrode; and a first magnetic layer provided between the first electrode and the second electrode and having magnetization in a first direction. The mounting substrate includes: a base; a first electrode pad provided on the base; and a second electrode pad provided on the base and provided apart from the first electrode pad. The method further includes joining the first electrode pad to the first electrode while heated, and joining the second electrode pad to the second electrode while heated, with an external magnetic field along the first direction applied to the sensor unit.

20 Claims, 13 Drawing Sheets

(56) References Cited

U.S. PATENT DOCUMENTS

| | | |
|---|---|---|
| 8,760,154 B2* | 6/2014 | Giddings et al. ............. 324/209 |
| 2003/0049865 A1* | 3/2003 | Santini et al. ................ 436/518 |
| 2003/0107832 A1* | 6/2003 | Morenzin et al. .............. 360/40 |
| 2008/0122572 A1* | 5/2008 | Jen et al. ........................ 338/2 |
| 2009/0162698 A1* | 6/2009 | Fukuzawa et al. ......... 428/811.2 |
| 2010/0127698 A1* | 5/2010 | Shimada et al. ............. 324/209 |
| 2011/0295128 A1 | 12/2011 | Yuasa et al. |
| 2012/0079887 A1 | 4/2012 | Giddings et al. |

OTHER PUBLICATIONS

U.S. Appl. No. 14/047,108, filed Oct. 7, 2013, Fukuzawa, et al.
U.S. Appl. No. 13/927,886, filed Jun. 26, 2013, Fuji, et al.

* cited by examiner

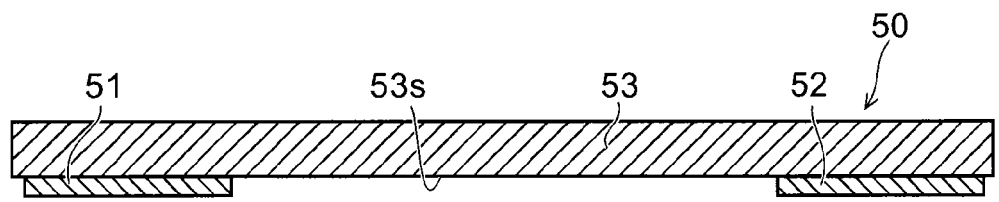
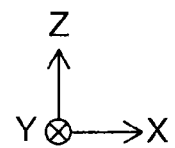
FIG. 4A
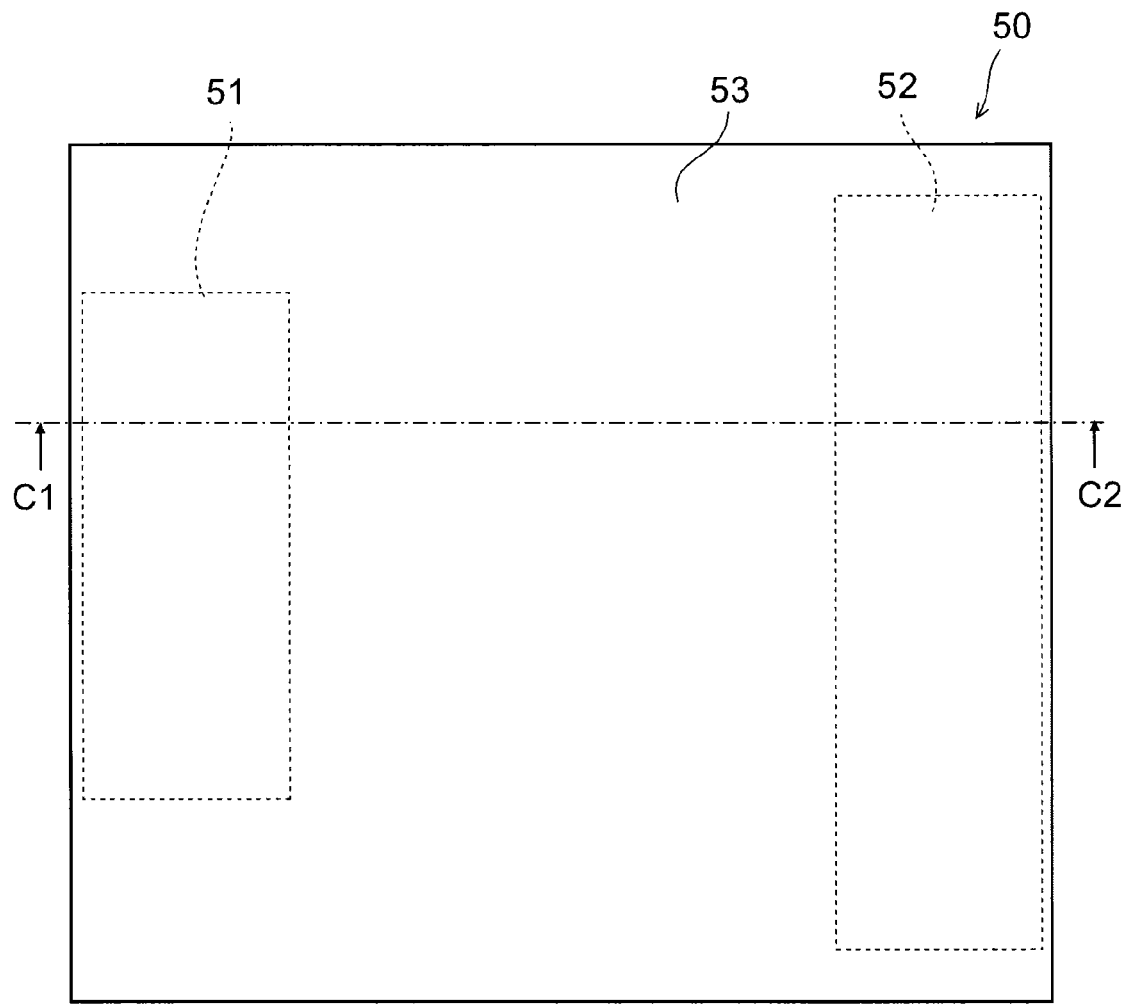
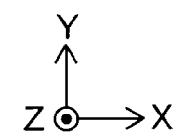
FIG. 4B

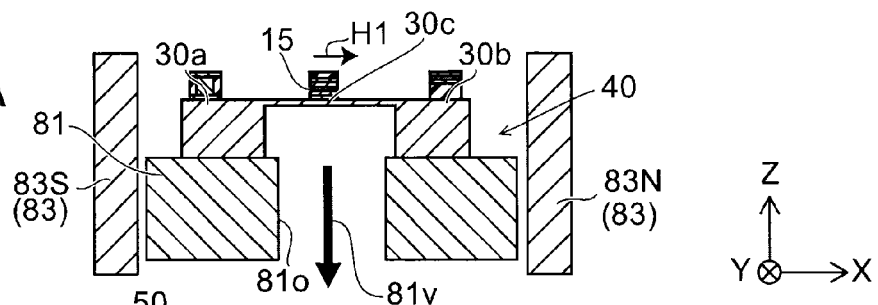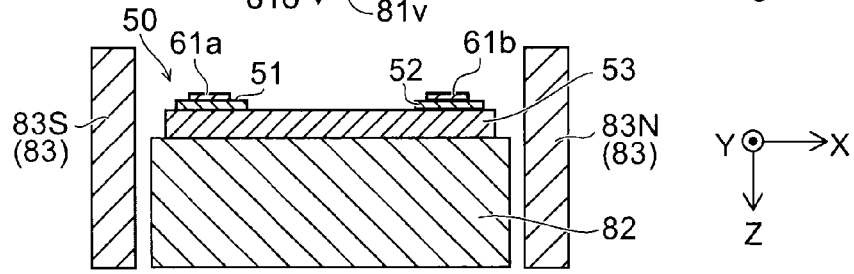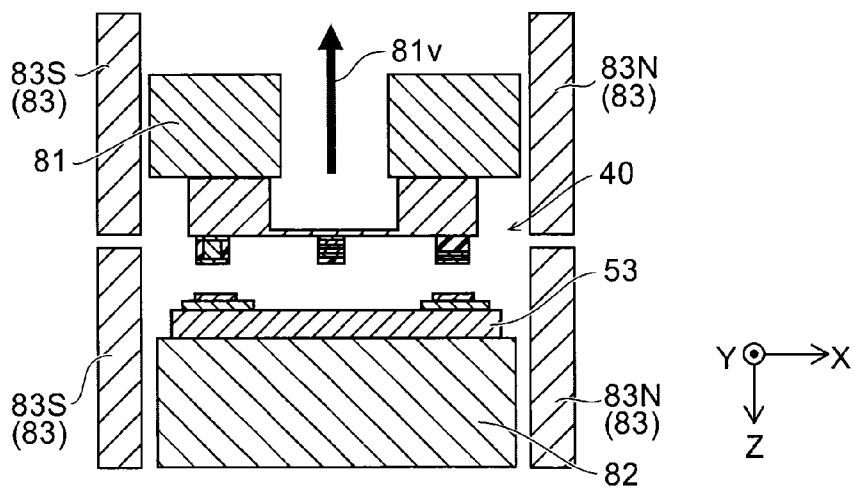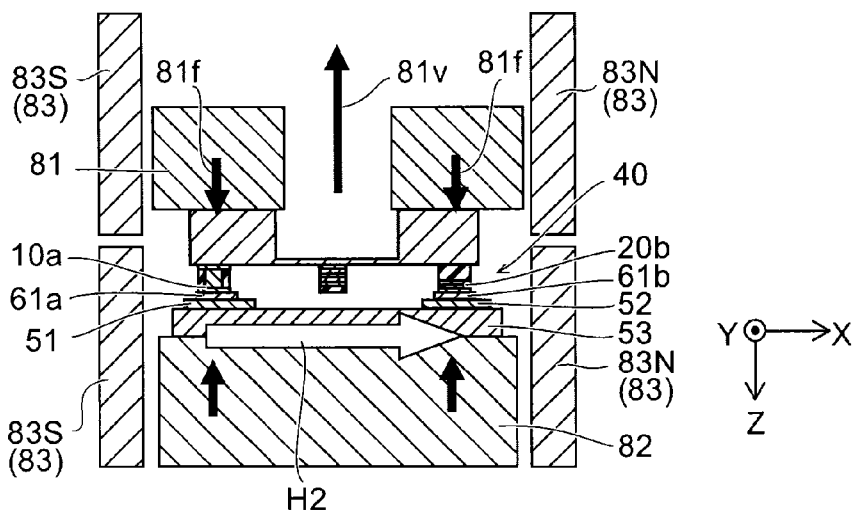

METHOD FOR MANUFACTURING PRESSURE SENSING DEVICE

CROSS-REFERENCE TO RELATED APPLICATIONS

This application is based upon and claims the benefit of priority from the prior Japanese Patent Application No. 2012-075148, filed on Mar. 28, 2012; the entire contents of which are incorporated herein by reference.

FIELD

Embodiments described herein relate generally to a method for manufacturing pressure sensing device.

BACKGROUND

There is a pressure sensing device using a magneto-resistive effect device. In the manufacturing processes of a pressure sensing device, a magneto-resistive effect device is disposed on a mounting substrate, and an electrode pad of the mounting substrate is connected to an electrode connected to the magneto-resistive effect device, for example. When a load is applied to the magneto-resistive effect device caused by various factors in the manufacturing processes, it is likely to reduce the sensitivity of the magneto-resistive effect device.

BRIEF DESCRIPTION OF THE DRAWINGS

FIG. 4A and FIG. 4B are schematic views illustrating a configuration of a mounting substrate of the pressure sensing device according to the first embodiment;

FIG. 5A to FIG. 5D are schematic cross-sectional views illustrating process steps of a method for manufacturing the pressure sensing device according to the first embodiment;

DETAILED DESCRIPTION

Figure 1:
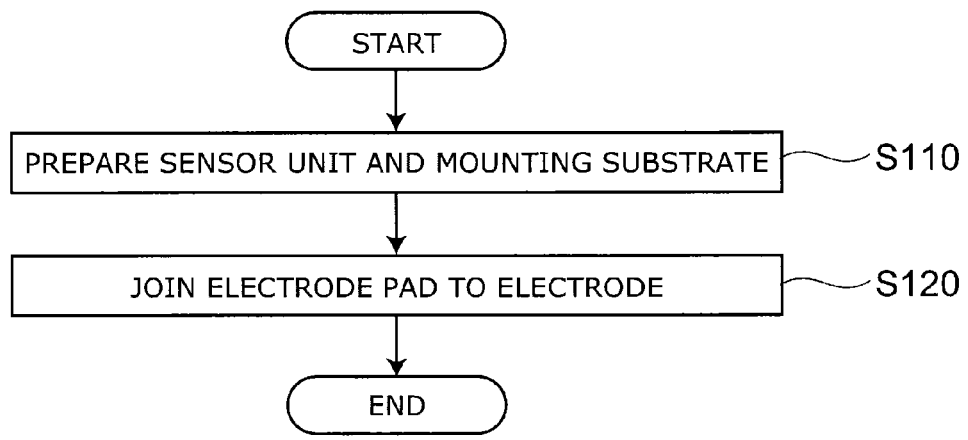
FIG. 1 is a flowchart illustrating a method for manufacturing a pressure sensing device according to a first embodiment.

In general, according to one embodiment, a method for manufacturing a pressure sensing device includes preparing a sensor unit and a mounting substrate. The sensor unit includes: a membrane body; and an element unit provided on the membrane body. The element unit includes: a first electrode; a second electrode; and a first magnetic layer provided between the first electrode and the second electrode and having magnetization in a first direction. The mounting substrate includes: a base; a first electrode pad provided on the base; and a second electrode pad provided on the base and provided apart from the first electrode pad. The method further includes joining the first electrode pad to the first electrode while heated, and joining the second electrode pad to the second electrode while heated, with an external magnetic field along the first direction applied to the sensor unit.

In general, according to another embodiment, a method for manufacturing a pressure sensing device includes: preparing a sensor unit and a mounting substrate, the sensor unit including: a membrane body; and an element unit provided on the membrane body, the element unit including: a first electrode having a first portion and a second portion; a second electrode having a third portion and a fourth portion; a first magnetic layer provided between the second portion and the third portion and having magnetization in a first direction; a second magnetic layer provided between the first magnetic layer and the third portion; and a non-magnetic layer provided between the first magnetic layer and the second magnetic layer, an angle between a magnetization direction of the first magnetic layer and a magnetization direction of the second magnetic layer being changed according to a strain of the membrane body; the mounting substrate including: a base; a first electrode pad provided on the base; and a second electrode pad provided on the base and provided apart from the first electrode pad; and joining the first electrode pad to the first portion while heated, and joining the second electrode pad to the fourth portion while heated, with an external magnetic field along the first direction applied to the sensor unit.

Various embodiments will be described hereinafter with reference to the accompanying drawings.

It is noted that the drawings are schematic or conceptual. The relationship between the thicknesses and widths of portions, a ratio of size between portions, or the like are not necessarily the same as real ones. Moreover, even in the case of expressing the same portions, dimensions and ratios between the portions are sometimes expressed differently depending on the drawings.

In the specification and drawings, components similar to those described or illustrated in a drawing thereinabove are marked with the identical reference numerals, and a detailed description is omitted as appropriate.

First Embodiment

FIG. 1 is a flowchart illustrating a method for manufacturing a pressure sensing device according to a first embodiment.

The pressure sensing device according to the embodiment includes a sensor unit having an electrode and a mounting substrate having an electrode pad. The manufacturing method includes the process step of preparing the sensor unit and the mounting substrate (Step S110) and the process step of joining the electrode pad to the electrode (Step S120).

In the following, an exemplary pressure sensing device, to which the manufacturing method according to the embodiment is applied, will be described.

The pressure sensing device according to the embodiment is applied to a blood pressure measurement device (for continuous blood pressure measurement, full time blood pressure measurement, or the like, for example), an acoustic pressure detector (a microphone or the like, for example), an atmospheric pressure gage, a vacuum gage (a pressure gage), a flow meter rate, or the like, for example.

Figure 2:
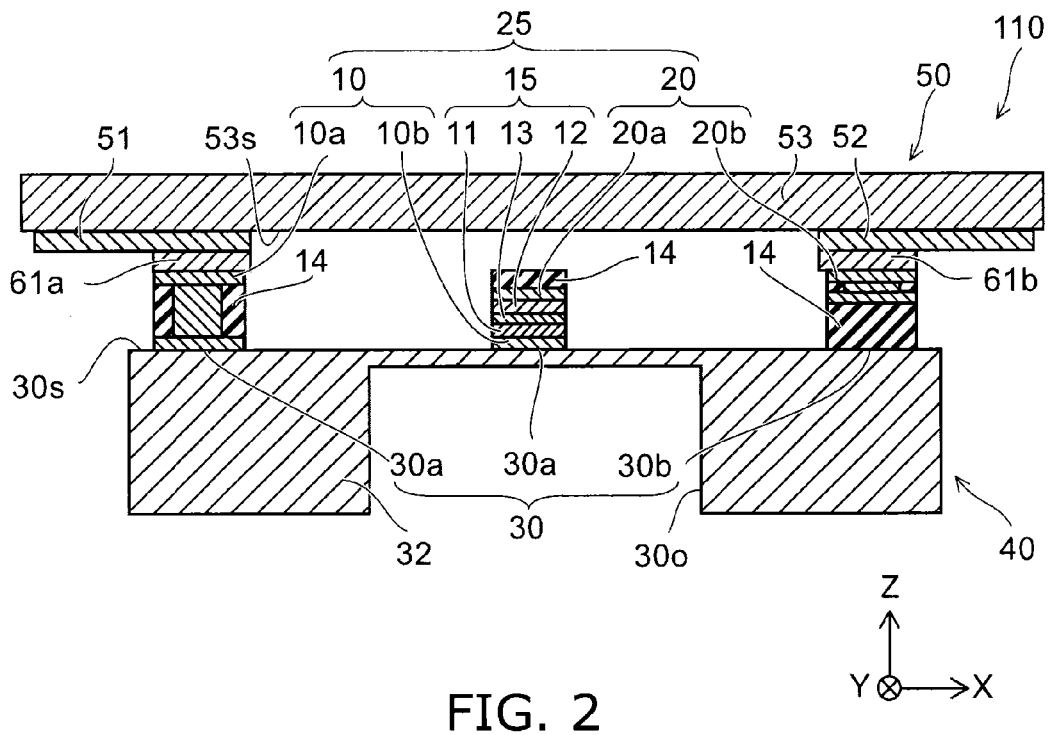
FIG. 2 is a schematic view illustrating a configuration of a pressure sensing device according to the first embodiment.

FIG. 2 is a schematic view illustrating the configuration of a pressure sensing device according to the first embodiment.

Figure 3A:
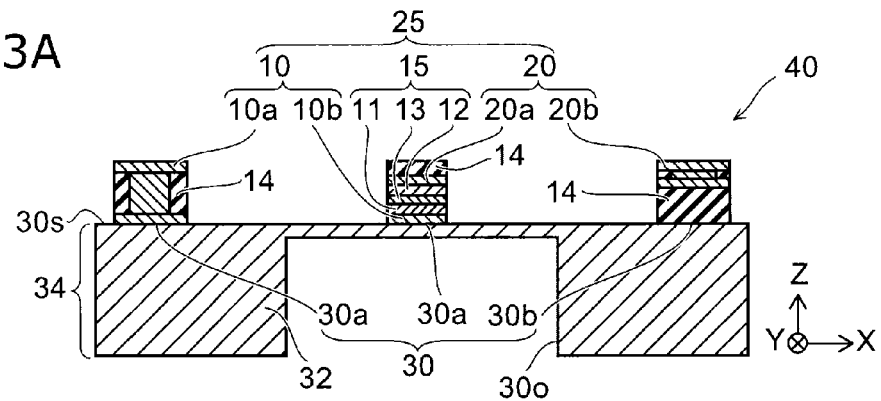
FIG. 3A to FIG. 3C are schematic views illustrating a configuration of a sensor unit of the pressure sensing device according to the first embodiment.
Figure 3B:
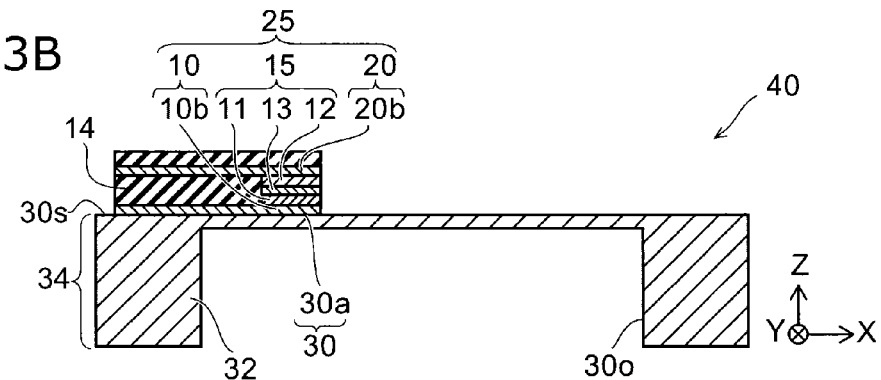
Figure 3C:
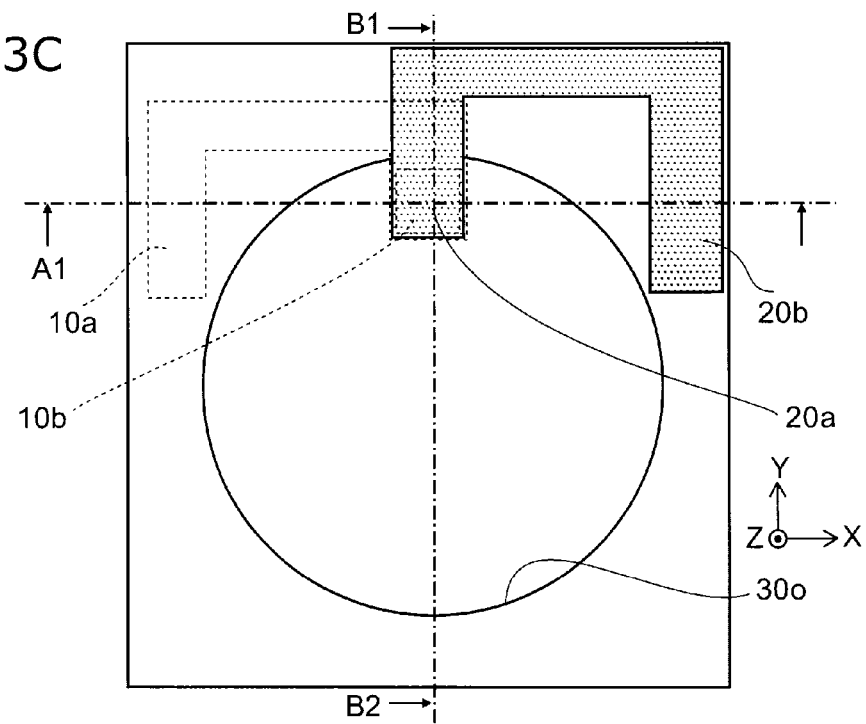

FIG. 3A to FIG. 3C are schematic views illustrating the configuration of a sensor unit of the pressure sensing device according to the first embodiment. FIG. 3C is a perspective plan view. FIG. 3A is a cross-sectional view along line A1-A2 in FIG. 3C. FIG. 3B is a cross-sectional view along line B1-B2 in FIG. 3C.

FIG. 4A and FIG. 4B are schematic views illustrating the configuration of a mounting substrate of the pressure sensing device according to the first embodiment. FIG. 4B is a perspective plan view. FIG. 4A is a cross-sectional view along line C1-C2 in FIG. 4B.

As shown in FIG. 3A to FIG. 3C, a sensor unit 40 includes a membrane body 30 and an element unit 25.

The membrane body 30 has a first major surface 30s. The first major surface 30s has a first edge portion 30a, a second edge portion 30b, and an inner side portion 30c. The second edge portion 30b is provided apart from the first edge portion 30a. The inner side portion 30c is located between the first edge portion 30a and the second edge portion 30b, for example.

Suppose that a direction vertical to the first major surface 30s is a Z-axis direction. A single direction vertical to the Z-axis direction is an X-axis direction. A direction vertical to the Z-axis direction and the X-axis direction is a Y-axis direction.

A membrane 34 is provided on the sensor unit 40, for example. The membrane 34 corresponds to the membrane body 30. A recess 30o is provided on a portion on the inner side of the membrane 34. The shape of the recess 30o when projected onto an X-Y plane is a circular shape (including a flat circle) or a polygon, for example. The recess 30o of the membrane 34 (a thin portion in the membrane 34) is the inner side portion 30c. The peripheral portion of the inner side portion 30c (a portion thicker than the recess 30o in the membrane 34, for example) is an outer side portion. One part of the outer side portion is the first edge portion 30a. The other part of the outer side portion is the second edge portion 30b. Silicon or the like is used for the membrane 34, for example. However, the embodiment is not limited thereto. The material of the membrane 34 is optional.

In this example, the thickness of the outer side portion of the membrane 34 is different from the thickness of the inner side portion 30c. The embodiment is not limited thereto. These thicknesses may be the same. In this example, although the shape of the membrane 34 is a rectangle, the shape is optional.

The element unit 25 is provided on the first major surface 30s. The element unit 25 includes a first electrode 10, a second electrode 20, a first magnetic layer 11, a second magnetic layer 12, and a non-magnetic layer 13.

The first electrode 10 has a first portion 10a and a second portion 10b. The first portion 10a opposes the first edge portion 30a. The second portion 10b opposes the inner side portion 30c.

In the specification, "to oppose" includes a state in which a component directly faces another component as well as a state in which a component faces another component with a different element inserted between the components.

The second electrode 20 has a third portion 20a and a fourth portion 20b. The third portion 20a opposes the inner side portion 30c. The fourth portion 20b opposes the second edge portion 30b. The fourth portion 20B does not overlap with the first electrode 10 when projected onto the X-Y plane (a plane parallel with the first major surface 30s).

The first magnetic layer 11 is provided between the second portion 10b and the third portion 20a. The first magnetic layer 11 has magnetization in a first direction.

The second magnetic layer 12 is provided between the first magnetic layer 11 and the third portion 20a.

The non-magnetic layer 13 is provided between the first magnetic layer 11 and the second magnetic layer 12.

The first magnetic layer 11, the non-magnetic layer 13, and the second magnetic layer 12 are stacked along the Z-axis direction.

In the specification, "to be stacked" includes a state in which components are directly stacked on each other as well as a state in which components are stacked on each other with a different element inserted between the components.

The first magnetic layer 11, the non-magnetic layer 13, and the second magnetic layer 12 form a strain sensing device 15. Namely, the element unit 25 includes the first electrode 10, the second electrode 20, and the strain sensing device 15. In the sensor unit 40, an angle between the magnetization direction of the first magnetic layer 11 and the magnetization direction of the second magnetic layer 12 is changed according to the strain of the membrane body 30. An exemplary configuration and exemplary characteristics of the strain sensing device 15 will be described later.

An insulating layer 14 where the strain sensing device 15 is buried is provided. $SiO_2$, $Al_2O_3$, or the like is used for the insulating layer 14, for example.

In this example, the second portion 10b of the first electrode 10, the first magnetic layer 11, the non-magnetic layer 13, the second magnetic layer 12, and the third portion 20a of the second electrode 20 are provided on the inner side portion 30c in this order. Namely, the second portion 10b is disposed between the third portion 20a and the inner side portion 30c. However, the embodiment is not limited thereto. The third portion 20a may be disposed between the second portion 10b and the inner side portion 30c, as described later.

As shown in FIG. 4A and FIG. 4B, the mounting substrate 50 includes a base 53, a first electrode pad 51, and a second electrode pad 52. The base 53 has a second major surface 53s. The first electrode pad 51 is provided on the second major surface 53s. The second electrode pad 52 is provided on the second major surface 53s, and provided apart from the first electrode pad 51. The shapes of the base 53, the first electrode pad 51, and the second electrode pad 52 are optional.

As shown in FIG. 2, in the pressure sensing device 110, the sensor unit 40 and the mounting substrate 50 are disposed in such a way that the first major surface 30s opposes the second major surface 53s. The first electrode pad 51 is electrically connected to the first portion 10a of the first electrode 10. In this example, a first conducting member 61a is disposed between the first electrode pad 51 and the first portion 10a.

The first conducting member 61a joins the first electrode pad 51 to the first portion 10a. The second electrode pad 52 is electrically connected to the fourth portion 20b of the second electrode 20. In this example, a second conducting member 61b is disposed between the second electrode pad 52 and the fourth portion 20b. The second conducting member 61b joins the second electrode pad 52 to the fourth portion 20b.

In the specification, a state in which a first member is joined to a second member includes a state in which the first member is directly fixed to the second member, a state in which the second member is directly fixed to the first member, a state in which the first member is indirectly fixed to the second member through a third member, and a state in which the second member is indirectly fixed to the first member through the third member.

The first magnetic layer 11 has magnetization in the first direction. The first direction is optional.

For example, the first direction is parallel with the X-Y plane. Suppose that the configuration using this state is referred to as "an in-plane magnetization type". In the in-plane magnetization type, an in-plane magnetization film is used for the first magnetic layer 11. For example, the first direction is sometimes shifted from the direction parallel with the X-Y plane in the in-plane magnetization film caused by variations in the manufacturing process steps.

For example, the first direction is vertical to the X-Y plane. The configuration using this state is referred to as "a perpendicular magnetization type". In the perpendicular magnetization type, a perpendicular magnetization film is used for the first magnetic layer 11. For example, the first direction is sometimes sifted from the direction vertical to the X-Y plane in the perpendicular magnetization film caused by variations in the manufacturing process steps.

For example, the first magnetic layer 11 functions as a reference layer. The second magnetic layer 12 functions as a free layer. In the free layer, the magnetization direction tends to be changed by an external magnetic field. The magnetization direction of the reference layer does not tend to be changed as compared with the magnetization direction of the free layer, for example. The reference layer is a pinned layer, for example. Both of the first magnetic layer 11 and the second magnetic layer 12 may be free layers.

For example, when stress is applied to a ferromagnetic body, an inverse magnetostrictive effect occurs in the ferromagnetic body. Stress applied to the strain sensing device 15 changes the magnetization direction of the magnetic layer based on the inverse magnetostrictive effect. An angle between the magnetization direction of the first magnetic layer 11 and the magnetization direction of the second magnetic layer 12 is changed to vary the electrical resistance of the strain sensing device 15 caused by MR (magnetoresistive) effect, for example.

In the pressure sensing device 110, stress applied to the pressure sensing device 110 causes displacement in the membrane body 30, the displacement applies stress to the strain sensing device 15, and the electrical resistance of the strain sensing device 15 is varied. The pressure sensing device 110 detects stress using this effect.

In the pressure sensing device 110, the sensor unit 40 is combined with the mounting substrate 50 in the mounting process step. In combining them, the sensor unit 40 is held in order to fix the position of the sensor unit 40, and the electrode pad is electrically connected to the electrode. In order to obtain a highly reliable connection, the electrode pad is connected to the electrode while heated.

The inventors found a fact that when the sensor unit 40 with excellent characteristics is combined with the mounting substrate 50, the characteristics of the sensor unit 40 are not always excellent. Namely, the characteristics of the tensor unit 40 are changed before and after the mounting process step. It was found that the characteristics deteriorate after the mounting process step even in the sensor unit 40 with excellent characteristics. When the characteristics deteriorate, it is difficult to detect stress highly sensitively. As the result of analysis, it was revealed that this deterioration is caused by a change in the magnetization direction of the magnetic layer because stress is applied to the sensor unit 40 when the sensor unit 40 is held in the mounting process step and the sensor unit 40 is heated while applying this stress.

The manufacturing method according to the embodiment solves a problem newly found in the manufacture of the pressure sensing device 110. The manufacturing method according to the embodiment suppresses the deterioration of the characteristics of the sensor unit 40 in the assembly process step.

An exemplary manufacturing method according to the embodiment will be described.

FIG. 5A to FIG. 5D are schematic cross-sectional views illustrating the process steps of a method for manufacturing the pressure sensing device according to the first embodiment.

As shown in FIG. 5A, the sensor unit 40 is placed on a first stage 81. An opening 81o is provided in the first stage 81. The edge portions of the sensor unit 40 (the first edge portion 30a and the second edge portion 30b, for example) are located on portions where the opening 81o of the first stage 81 is not provided. The inner side portion 30c of the sensor unit 40 is located above the opening 81. The pressure in a space below the inner side portion 30c is reduced through the opening 81o. Force caused by a vacuum chuck 81v is applied to the inner side portion 30c, for example, for fixing the sensor unit 40 to the first stage 81. In this fixing, stress is applied to the inner side portion 30c of the sensor unit 40.

As described above, in the manufacturing method according to the embodiment, the first edge portion 30a and the second edge portion 30b of the sensor unit 40 are held in the process step of holding the sensor unit 40. In this holding, the inner side portion 30c is deformed. For example, in the holding process step, the inner side portion 30c is depressure-chucked while holding the first edge portion 30a and the second edge portion 30b. Therefore, the inner side portion 30c is sometimes deformed. The sensor unit 40 is held by depressure chucking, so that the sensor unit 40 can be held without contacting the functional unit of the sensor unit 40 (the strain sensing device 15 or the like), and the deterioration of the characteristics of the functional unit can be suppressed.

As shown in FIG. 5A, a magnetization direction H1 of the first magnetic layer 11 of the strain sensing device 15 is along the X-axis direction, for example. In this example, the strain sensing device 15 is an in-plane magnetization type device.

For example, the temperature of the first stage 81 is set at high temperature (at temperatures of 150° C. or more and 250° C. or less, for example), so that a high adhesion can be obtained in joining the electrode to the electrode pad through an ACF (Anisotropic Conductive Film) or ACP (Anisotropic Conductive Paste), for example, in the joining process step described later.

In the embodiment, a magnetic field applying unit 83 is also provided on the first stage 81. The magnetic field applying unit 83 has an S-pole portion 83S and an N-pole portion 83N, for example. The sensor unit 40 is disposed between the S-pole portion 83S and the N-pole portion 83N. In heating the sensor unit 40, the magnetic field applying unit 83 applies an external magnetic field H2 to the sensor unit 40. In the direction of the external magnetic field H2 is along the magnetization direction of the first magnetic layer 11. Namely, for example, the sensor unit 40 is heated while applying the external magnetic field H2 to the first magnetic layer 11.

As shown in FIG. 5B, the mounting substrate 50 is placed on a second stage 82. The first conducting member 61a is disposed on the first electrode pad 51 of the mounting substrate 50. The second conducting member 61b is disposed on the second electrode pad 52. A thermocompression bonding conductive material is used for the first conducting member 61a and the second conducting member 61b, for example. An ACF, ACP, or the like is used, for example.

In the embodiment, the magnetic field applying unit 83 is also provided on the second stage 82. The magnetic field applying unit 83 has the S-pole portion 83S and the N-pole portion 83N, for example. The mounting substrate 50 is disposed between the S-pole portion 83S and the N-pole portion 83N.

As shown in FIG. 5C, the sensor unit 40 is placed upside down, and the sensor unit 40 opposes the mounting substrate 50. The electrode of the sensor unit 40 is aligned with the electrode pad of the mounting substrate 50.

As shown in FIG. 5D, the first portion 10a of the first electrode 10 is brought close to the first electrode pad 51 of the mounting substrate 50, and the fourth portion 20b of the second electrode 10 is brought close to the second electrode pad 52 of the mounting substrate 50. A pressure 81f (a load) is applied, and the first portion 10a is joined to the first electrode pad 51 through the first conducting member 61a while heated. The pressure 81f is applied, and the fourth portion 20b is joined to the second electrode pad 52 through the second conducting member 61b while heated.

In the joining in the embodiment, the magnetic field applying unit 83 applies the external magnetic field H2 to the sensor unit 40 in the joining process step. The direction of the external magnetic field H2 is along the magnetization direction of the first magnetic layer 11, so that the sensor unit 40 is heated while applying the external magnetic field H2 to the first magnetic layer 11.

As described above, in the embodiment, the first electrode pad 51 is joined to the first portion 10a while heated with the external magnetic field H2 along the magnetization direction of the first magnetic layer 11 (in the first direction) applied to the sensor unit 40, and the second electrode pad 52 is joined to the fourth portion 20b while heated in the joining process step (Step S120).

Accordingly, a change in the magnetization of the first magnetic layer 11 in the joining process step can be suppressed, and a highly sensitive pressure sensing device can be manufactured in excellent production.

FIG. 6A to FIG. 6F are schematic views illustrating the characteristics of the pressure sensing device.

Figure 6A:
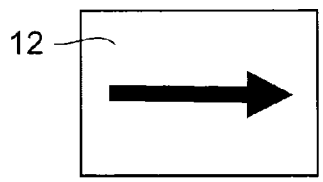
FIG. 6A to FIG. 6F are schematic views illustrating a characteristics of the pressure sensing device.
Figure 6B:
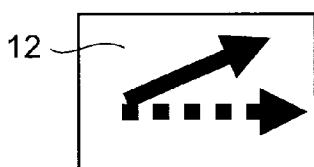
Figure 6C:
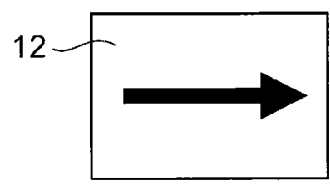
Figure 6D:
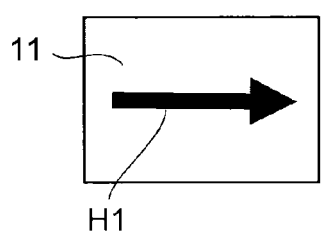
Figure 6E:
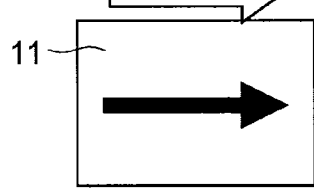
Figure 6F:
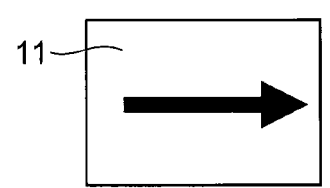

FIG. 6A to FIG. 6C illustrate characteristics when the manufacturing method according to the embodiment is applied. FIG. 6D to FIG. 6F illustrate characteristics when a manufacturing method according to a reference sample is applied. In the reference sample, the external magnetic field H2 is not applied in the assembly process step. FIG. 6A and FIG. 6D illustrate the states of the magnetization of the magnetic layer before the assembly process step or when the sensor unit 40 is held. FIG. 6B and FIG. 6E illustrate the states of the magnetization of the magnetic layer at high temperature in joining the electrode pad to the electrode. FIG. 6C and FIG. 6F illustrate the states of the magnetization of the magnetic layer after finishing joining and the assembly process step.

As shown in FIG. 6D, before the assembly process step, the magnetization direction H1 of the first magnetic layer 11 is directed to a predetermined direction. In this example, the magnetization direction of the second magnetic layer 12 is parallel with the magnetization direction H1 of the first magnetic layer 11. However, in the embodiment, the magnetization direction of the second magnetic layer 12 is optional. Also in the state in which the sensor unit 40 is held and the sensor unit 40 is deformed, the magnetization direction of the first magnetic layer 11 is not changed when the temperature of the sensor unit 40 is low.

As illustrated in FIG. 6E, in the process step of joining the electrode pad to the electrode, the temperature of the magnetic layer becomes high. The sensor unit 40 is deformed, and the temperature is high. Therefore, in the reference sample, the magnetization direction of the first magnetic layer is changed from the initial magnetization direction H1. Namely, heat and strain in the joining process step change the magnetization direction of the first magnetic layer 11. In this example, the magnetization direction of the second magnetic layer 12 is also changed from the initial state.

As shown in FIG. 6F, when joining is finished and the temperature becomes at ambient temperature, the magnetization direction of the first magnetic layer 11 is fixed in the state changed from the initial magnetization direction H1.

As described above, in the reference sample, heat and strain in the joining process step change the magnetization direction of a single magnetic layer 11 from the state before the assembly process step. Therefore, in the manufacturing method according to the reference sample, the characteristics of the pressure sensing device deteriorate.

As shown in FIG. 6A, also in the manufacturing method according to the embodiment, before the assembly process step and in the state in which the sensor unit 40 is held and the sensor unit 40 is deformed, the magnetization direction H1 of the first magnetic layer 11 is directed to a predetermined direction. In the case where the temperature of the sensor unit 40 is low, the magnetization direction of the first magnetic layer 11 is not changed. This state is the same as the state in the reference sample.

As shown in FIG. 6B, the external magnetic field H2 along the initial magnetization direction H1 of the first magnetic layer 11 is applied at high temperature in joining the electrode pad to the electrode and in the state in which the sensor unit 40 is deformed. In the embodiment, the external magnetic field H2 maintains the initial magnetization direction H1 in the magnetization direction of the first magnetic layer 11.

Therefore, as shown in FIG. 6C, when joining is finished and the temperature becomes at ambient temperature, the initial magnetization direction H1 is maintained in the magnetization direction of the first magnetic layer 11.

As described above, in the manufacturing method according to the embodiment, the external magnetic field H2 is applied when heat and strain are applied in the joining process step, so that a change in the magnetization direction of the first magnetic layer 11 is suppressed from the state before the assembly process step. Accordingly, in the manufacturing method according to the embodiment, the characteristics of the pressure sensing device do not deteriorate, and a highly sensitive pressure sensing device can be manufactured.

For example, in the joining process steps illustrated in FIG. 6B and FIG. 6E, the temperature of a solderless terminal is a temperature of 200° C. or more, for example. Therefore, in the joining process step, the temperature of the magnetic layer is increased to a blocking temperature or a temperature close to the blocking temperature. The blocking temperature is at a temperature at which the exchange coupling of an antiferromagnetic body that fixes the magnetization of the first magnetic layer 11 (a reference layer, for example) is substantially gone. Exchange coupling becomes weak around the blocking temperature. When exchange coupling becomes weak, stress is applied to the first magnetic layer 11 in the direction of rotating the magnetization of the first magnetic layer 11, strain occurs in the first magnetic layer 11, and the components of the magnetization of the first magnetic layer 11 are then partially rotated in the direction. When the first magnetic layer 11 is cooled in this state, the magnetization direction of the first magnetic layer 11 is fixed. In the joining process step, since the sensor unit 40 is fixed using a vacuum chuck unit, for example, stress is applied to the magnetic layer.

It was revealed from various experiments conducted by the inventors that the magnetization direction of the magnetic layer fluctuates in the case where the external magnetic field H2 is not applied. As a result, the fixing magnetic field of the first magnetic layer 11 becomes weak. Therefore, when operating the device, the magnetization of the first magnetic layer tends to be rotated by an external pressure, and the device does not operate stably. The MR change rate is reduced, and output is reduced.

More particularly, since a thermosetting resin is used for an ACF or ACP in joining using an ACF or ACP, heat is applied while applying a pressure. Because of the heat and the pressure, it was revealed that the sensor unit 40 is deformed by the vacuum chuck unit holding the sensor unit 40 as well as the sensor unit 40 is deformed by applying a pressure to cause strain in the sensor unit 40, and that the strain causes the magnetization direction of the magnetic layer to more tend to be changed in the joining process step. When using an ACF or ACP, the exchange coupling of the first magnetic layer 11 becomes further weak, and the magnetization of the first magnetic layer 11 further tends to be rotated.

In the manufacturing method according to the embodiment, in the joining process step, the external magnetic field H2 along the initial magnetization direction H1 of the first magnetic layer 11 is applied in the state in which stress is applied as the temperature of the sensor unit 40 is high. Accordingly, the external magnetic field H2 can maintain the magnetization direction of the first magnetic layer 11 in a predetermined direction, even though heat and stress are applied to the first magnetic layer 11 and force to rotate magnetization due to strain works in the joining process step.

As described in FIG. 5A, in the case where the sensor unit 40 is heated in the process step of holding the sensor unit 40, preferably, the external magnetic field H2 is applied to the sensor unit 40 in the process step.

The external magnetic field H2 (the strength of the external magnetic field H2) is greater than the saturation magnetic field of the first magnetic layer 11, for example. Accordingly, a change in the magnetization direction of the first magnetic layer 11 when applying heat and stress to the first magnetic layer 11, for example, can be effectively suppressed.

The value of the external magnetic field H2 is the value of the exchange coupling magnetic field of the first magnetic layer 11 or more, for example. Accordingly, a change in the magnetization direction of the first magnetic layer 11 when applying heat and stress to the first magnetic layer 11, for example, can be effectively suppressed.

In operating the pressure sensing device 110, in the case where the magnetization direction of the first magnetic layer 11 is substantially fixed (in the case where the first magnetic layer 11 is a pinned layer), the external magnetic field H2 is 500 oersteds (Oe) or more, for example.

In operating the pressure sensing device 110, in the case where the magnetization direction of the first magnetic layer 11 is changed (in the case where the first magnetic layer 11 is a free layer), the external magnetic field H2 is 10 Oe or more, for example.

Preferably, the external magnetic field H2 is 3,000 Oe or less. When the external magnetic field H2 exceeds 3,000 Oe, the magnetic field applying unit 83 is increased in size. The external magnetic field H2 at 3,000 Oe or less can sufficiently suppress a change in the magnetization direction of the first magnetic layer 11 when stress is applied at high temperature.

The external magnetic field H2 is applied using a permanent magnet, for example. Namely, a permanent magnet can be used for the magnetic field applying unit 83. An Al—Ni—Co magnet, a ferrite magnet, a samarium-cobalt magnet, a neodymium magnet, or the like can be used for the permanent magnet.

The external magnetic field H2 is applied using an electromagnet, for example. Namely, an electromagnet can be used for the magnetic field applying unit 83. Preferably, the electromagnet includes a quadrupole field generating coil. In the embodiment, a method for applying the external magnetic field H2 is optional.

For example, in the embodiment, the first electrode pad 51 is joined to the first portion 10a in the joining process step, in which a first conductive adhesive layer (such as an ACF and ACP) is inserted between the first electrode pad 51 and the first portion 10a and the pressure 81f is applied to the first electrode pad 51 and the first portion 10a while heated for joining the first electrode pad 51 to the first portion 10a, for example.

For example, the second electrode pad 52 is joined to the fourth portion 20b, in which a second conductive adhesive layer is inserted between the second electrode pad 52 and the fourth portion 20b and the pressure 81f is applied to the second electrode pad 52 and the fourth portion 20b while heated for joining the second electrode pad 52 to the fourth portion 20b.

The pressure 81f is applied for joining using the conductive adhesive layers to obtain more reliable electric characteristics. In the joining process step in which the pressure 81f is applied while heated, a change in the magnetization direction of the magnetic layer can be suppressed by applying the external magnetic field H2.

Figure 7:
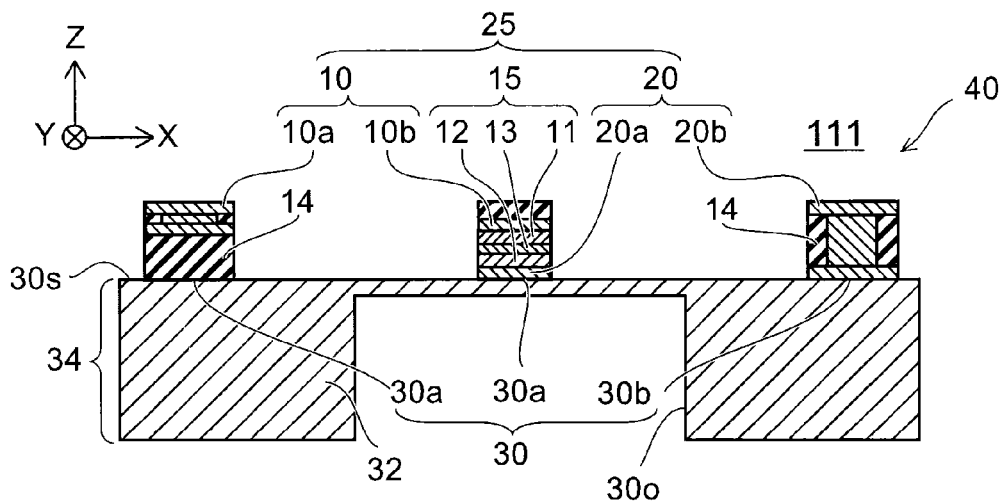
FIG. 7 is a schematic cross-sectional view illustrating a configuration of a sensor unit of another pressure sensing device.

FIG. 7 is a schematic cross-sectional view illustrating the configuration of a sensor unit of another pressure sensing device according to the first embodiment.

FIG. 7 is a cross-sectional view corresponding to the cross section along line A1-A2 in FIG. 3C.

As shown in FIG. 7, in a sensor unit 40 of a pressure sensing device 111 according to the embodiment, a third portion 20a of a second electrode 20 is provided on a membrane body 30. A second magnetic layer 12 is provided on the third portion 20a. A non-magnetic layer 13 is provided on the second magnetic layer 12. A first magnetic layer 11 is provided on the non-magnetic layer 13. A second portion 10b of a first electrode 10 is provided on the first magnetic layer 11. As described above, in this example, the third portion 20a is disposed between the second portion 10b and the inner side portion 30. Also in this case, a first portion 10a of the first electrode 10 is provided on a first edge portion 30a, and a fourth portion 20b of the second electrode 20 is provided on a second edge portion 30b. Also in the pressure sensing device 111, the manufacturing method according to the embodiment can be applied. Accordingly, a highly sensitive pressure sensing device can be manufactured.

Figure 8A:
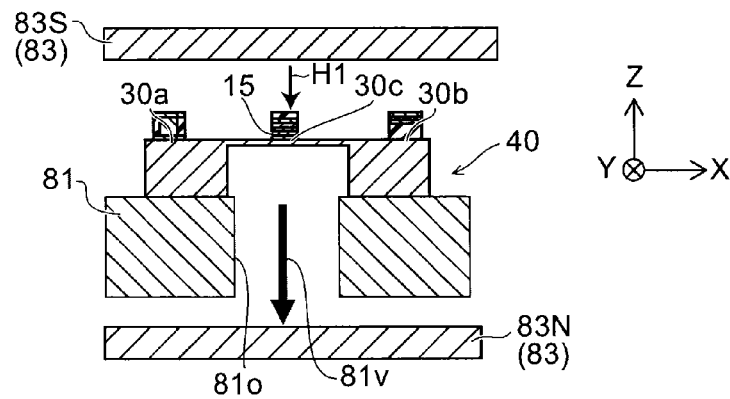
FIG. 8A to FIG. 8C are schematic cross-sectional views illustrating process steps of another method for manufacturing the pressure sensing device according to the first embodiment.
Figure 8B:
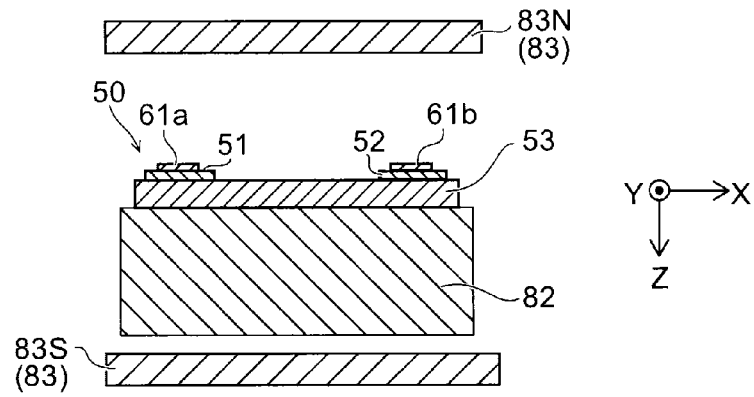
Figure 8C:
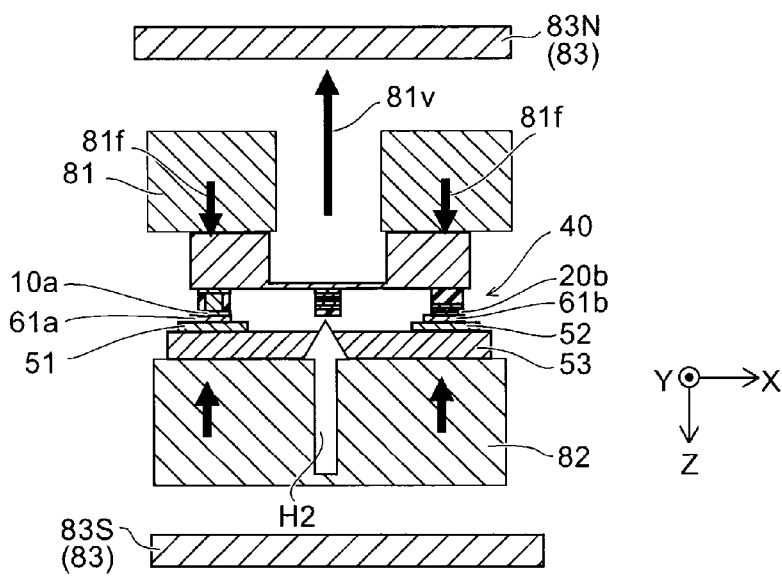

FIG. 8A to FIG. 8C are schematic cross-sectional views illustrating the process steps of another method for manufacturing the pressure sensing device according to the first embodiment.

As shown in FIG. 8A, the sensor unit 40 is placed on the first stage 81. The first edge portion 30a and the second edge portion 30b of the sensor unit 40 are held. In this holding, there is also the case where the sensor unit 40 is held as the inner side portion 30c is deformed. For example, in the holding process step, the inner side portion 30c is depressure-chucked, and the inner side portion 30c is deformed while holding the first edge portion 30a and the second edge portion 30b. In this example, the magnetization direction H1 of the first magnetic layer 11 of the strain sensing device 15 is directed to the Z-axis direction, for example. In this example, the strain sensing device 15 is a perpendicular magnetization type device. In the case where the sensor unit 40 is heated in the process step, the magnetic field applying unit 83 applies the external magnetic field H2 to the sensor unit 40. The direction of the external magnetic field H2 is along the magnetization direction H1 of the first magnetic layer 11.

As shown in FIG. 8B, the mounting substrate 50 is placed on the second stage 82. The first conducting member 61a is disposed on the first electrode pad 51 of the mounting substrate 50. The second conducting member 61b is disposed on the second electrode pad 52.

In the embodiment, the magnetic field applying unit 83 generates the external magnetic field H2 in the Z-axis direction. The mounting substrate 50 is disposed between the S-pole portion 83S and the N-pole portion 83N of the magnetic field applying unit 83. The S-pole portion 83S opposes the N-pole portion 83N along the Z-axis direction.

As shown in FIG. 8C, the sensor unit 40 is placed upside down, and the sensor unit 40 opposes the mounting substrate 50. The first portion 10a of the first electrode 10 is brought close to the first electrode pad 51 of the mounting substrate 50, and the fourth portion 20b of the second electrode 10 is brought close to the second electrode pad 52 of the mounting substrate 50. The pressure 81f is then applied while heated, and the first portion 10a is joined to the first electrode pad 51 through the first conducting member 61a. The pressure 81f is applied while heated, and the fourth portion 20b is joined to the second electrode pad 52 through the second conducting member 61b.

In the joining process step, the magnetic field applying unit 83 applies the external magnetic field H2 along the Z-axis direction to the sensor unit 40. The direction of the external magnetic field H2 is along the magnetization direction of the first magnetic layer 11, so that the sensor unit 40 is heated while applying the external magnetic field H2 to the first magnetic layer 11. Accordingly, a change in the magnetization of the first magnetic layer 11 in the joining process step can be suppressed, and a highly sensitive pressure sensing device can be manufactured in excellent production.

In the embodiment, the external magnetic field H2 is set substantially in parallel with the magnetization direction H1 of the first magnetic layer 11, and the external magnetic field H2 is set as matched with the magnetization direction H1 of the first magnetic layer 11. The absolute value of an angle between the direction of the external magnetic field H2 and the magnetization direction H1 of the first magnetic layer 11 is an angle of 10 degrees or less, for example.

Figure 9A:
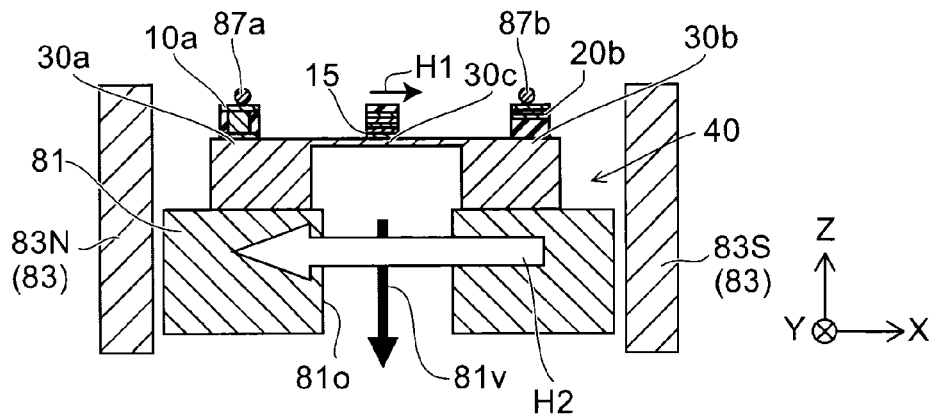
FIG. 9A to FIG. 9C are schematic cross-sectional views illustrating process steps of still another method for manufacturing the pressure sensing device according to the first embodiment.
Figure 9B:
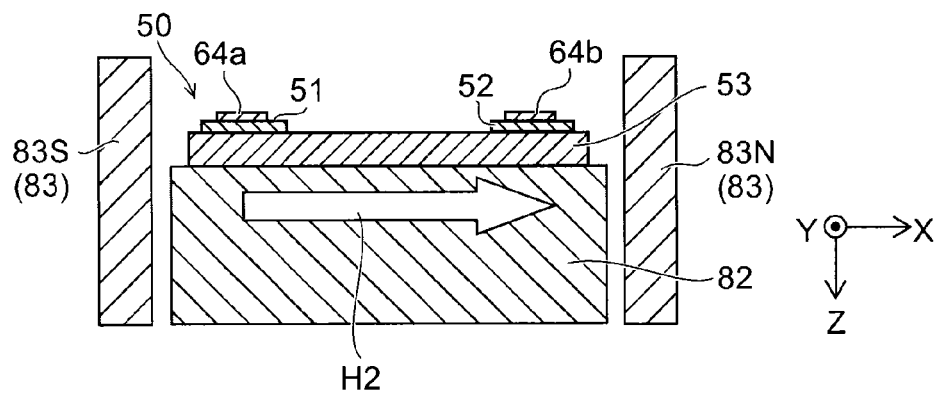
Figure 9C:
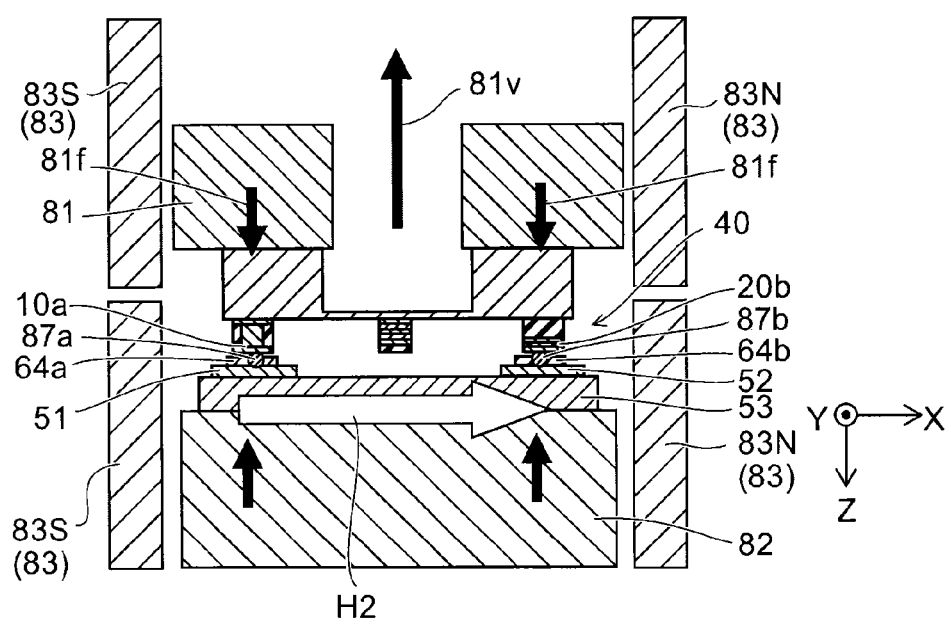

FIG. 9A to FIG. 9C are schematic cross-sectional views illustrating the process steps of still another method for manufacturing the pressure sensing device according to the first embodiment.

In this example, a bump and a thermosetting resin are used for joining.

As shown in FIG. 9A, the sensor unit 40 is placed on the first stage 81. The first edge portion 30a and the second edge portion 30b of the sensor unit 40 are held. In this holding, there is also the case where the sensor unit 40 is held with the inner side portion 30c deformed. For example, in the holding process step, the inner side portion 30c is depressure-chucked, and the inner side portion 30c is deformed while holding the first edge portion 30a and the second edge portion 30b. In this example, the magnetization direction H1 of the first magnetic layer 11 of the strain sensing device 15 is directed to a direction vertical to the Z-axis direction, for example.

In this example, the magnetic field applying unit 83 generates the external magnetic field H2 in this state. The direction of the external magnetic field H2 is along the magnetization direction of the first magnetic layer 11. The first stage 81 is heated at temperatures of about 100° C. or more and 180° C. or less, for example. In this state, a first bump 87a (a gold bump, for example) is formed on the first portion 10a of the first electrode 10, and a second bump 87b (a gold bump, for example) is formed on the fourth portion 20b of the second electrode 20. Since the first stage 81 is heated, excellent connections can be obtained between the first bump 87a and the first portion 10a and between the second bump 87b and the fourth portion 20b.

In the process step of forming the bumps as described above, the temperature becomes high in the state in which the inner side portion 30c is deformed, for example. However, since the external magnetic field H2 is applied, a change in the magnetization of the first magnetic layer 11 in the joining process step can be suppressed.

As shown in FIG. 9B, the mounting substrate 50 is placed on the second stage 82. A first thermoset resin layer 64a is disposed on the first electrode pad 51 of the mounting substrate 50. A second thermoset resin layer 64b is disposed on the second electrode pad 52. In this stage, the thermoset resin layers are not cured enough. The first thermoset resin layer 64a and the second thermoset resin layer 64b are insulative.

As shown in FIG. 9C, the sensor unit 40 is placed upside down, and the sensor unit 40 opposes the mounting substrate 50. The first portion 10a of the first electrode 10 is brought close to the first electrode pad 51 of the mounting substrate 50, and the fourth portion 20b of the second electrode 10 is brought close to the second electrode pad 52 of the mounting substrate 50. The first bump 87a penetrates through the first thermoset resin layer 64a, and contacts the first electrode pad 51. The second bump 87b penetrates through the second thermoset resin layer 64b, and contacts the second electrode pad 52. The pressure 81f is then applied while heated, and the first portion 10a is joined to the first electrode pad 51 through the first bump 87a. The pressure 81f is applied while heated, and the fourth portion 20b is joined to the second electrode pad 52 through the second bump 87b. This heating cures the first thermoset resin layer 87a and the second thermoset resin layer 87b, and the mechanical strength of joining is increased.

As described above, joining the first electrode pad 51 to the first portion 10a includes inserting the first conducting member (the first bump 87a) and the first thermoset resin layer 64a provided around the first conducting member between the first electrode pad 51 and the first portion 10a, applying a pressure across the first electrode pad 51 and the first portion 10a while heated, and joining the first electrode pad 51 to the first portion 10a. Joining the second electrode pad 52 to the fourth portion 20b includes inserting the second conducting member (the second bump 87b) and the second thermoset resin layer 64b provided around the second conducting member between the second electrode pad 52 and the fourth portion 20b, applying a pressure across the second electrode pad 52 and the fourth portion 20b while heated, and joining the second electrode pad 52 to the fourth portion 20b.

Also in the joining process steps, the magnetic field applying unit 83 applies the external magnetic field H2 to the sensor unit 40. The direction of the external magnetic field H2 is along the magnetization direction of the first magnetic layer 11, so that the sensor unit 40 is heated while applying the external magnetic field H2 to the first magnetic layer 11. Accordingly a change in the magnetization of the first magnetic layer 11 in the joining process step can be suppressed, and a highly sensitive pressure sensing device can be manufactured in excellent production.

Although this example is the case of an in-plane magnetization type device, the bumps and the thermosetting resins may be used for joining in a perpendicular magnetization type device. Also in this case, the external magnetic field H2 is set substantially in parallel with the magnetization direction H1 of the first magnetic layer 11, and the direction is the Z-axis direction, for example.

An exemplary manufacturing method according to the embodiment will be described.

Figure 10A:
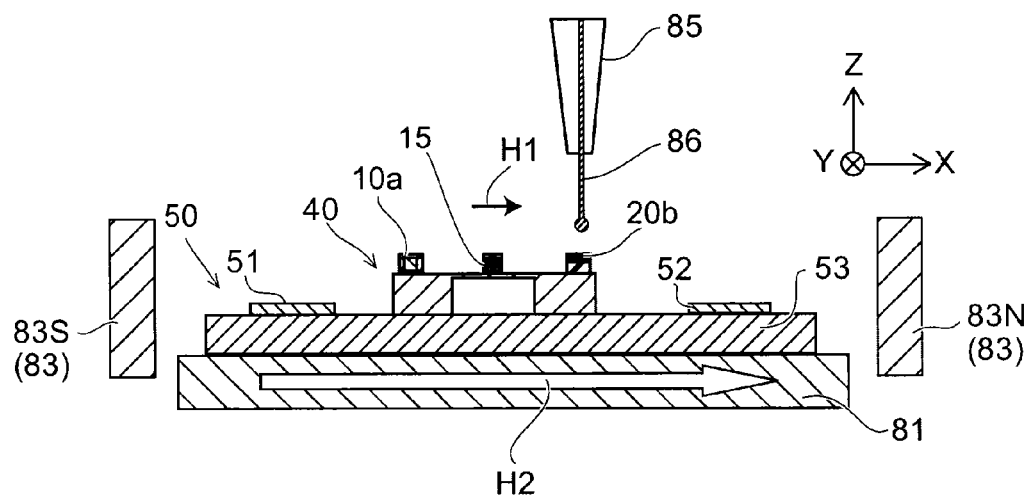
FIG. 10A and FIG. 10B are schematic cross-sectional views illustrating process steps of yet another method for manufacturing the pressure sensing device according to the first embodiment.
Figure 10B:
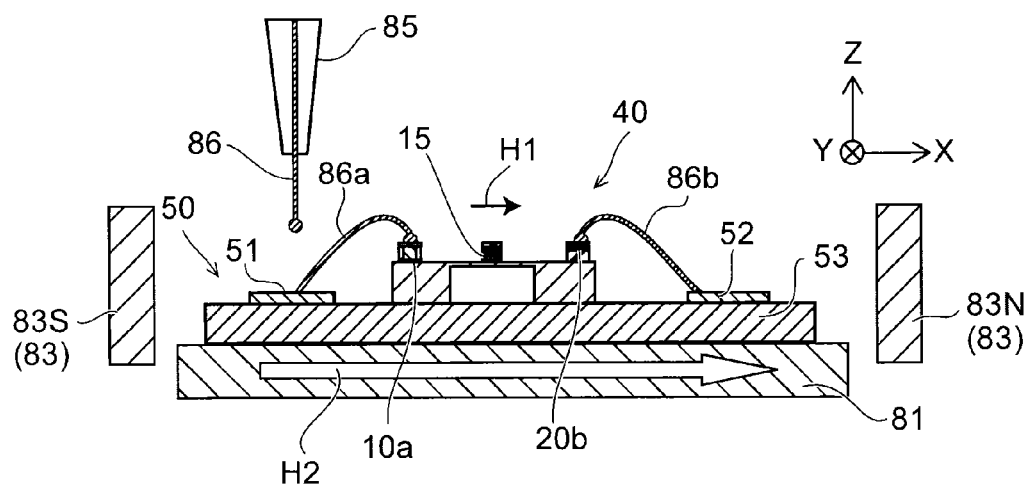

FIG. 10A and FIG. 10B are schematic cross-sectional views illustrating the process steps of yet another method for manufacturing the pressure sensing device according to the first embodiment.

In this example, wire bonding is used for joining.

As shown in FIG. 10A, the sensor unit 40 is disposed on the first stage 81.

In this example, the mounting substrate 50 is disposed on the first stage 81. The sensor unit 40 is disposed on the mounting substrate 50. In this example, the magnetization direction H1 of the first magnetic layer 11 is along the X-axis direction. The sensor unit 40 is held by depressure chucking, for example, and the sensor unit 40 is deformed, for example.

The first stage 81 is provided with the magnetic field applying unit 83. The external magnetic field H2 applied by the magnetic field applying unit 83 is along the X-axis direction (namely, the magnetization direction H1 of the first magnetic layer 11). The first stage 81 is provided with a capillary 85 that supplies an interconnect material 86. The capillary 85 is movable in the X-axis direction, the Y-axis direction, and the Z-axis direction. A gold line or the like is used for the interconnect material 86, for example.

As shown in FIG. 10B, joining is performed while applying the external magnetic field H2 to the sensor unit 40. In joining the first electrode pad 51 to the first portion 10a, a first interconnecting layer material 86a (the interconnect material 86) is joined to the first electrode pad 51 while heated, and the first interconnecting layer material 86a is joined to the first portion 10a while heated. In joining the second electrode pad 52 to the fourth portion 20b, a second interconnecting layer material 86b (the interconnect material 86) is joined to the second electrode pad 52 while heated, and the second interconnecting layer material 86 is joined to the fourth portion 20b while heated.

Also in the joining, heat and stress are applied to the first magnetic layer 11 when heating and joining the first interconnecting layer material 86a and the second interconnecting layer material 86b. In applying heat and stress, in the embodiment, a change in the magnetization direction of the first magnetic layer 11 from the initial direction can be suppressed by applying the external magnetic field H2.

Figure 11A:
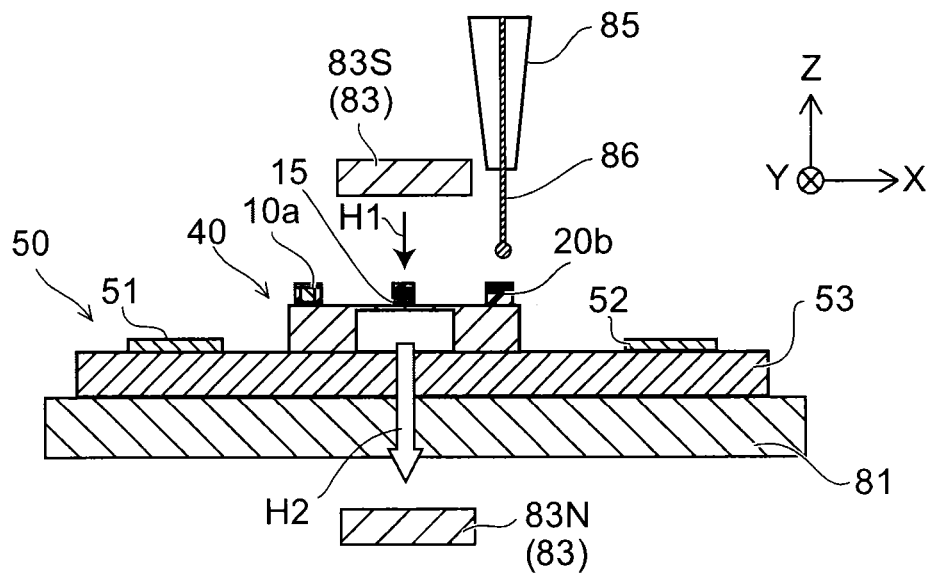
FIG. 11A and FIG. 11B are schematic cross-sectional views illustrating process steps of still yet another method for manufacturing the pressure sensing device according to the first embodiment.
Figure 11B:
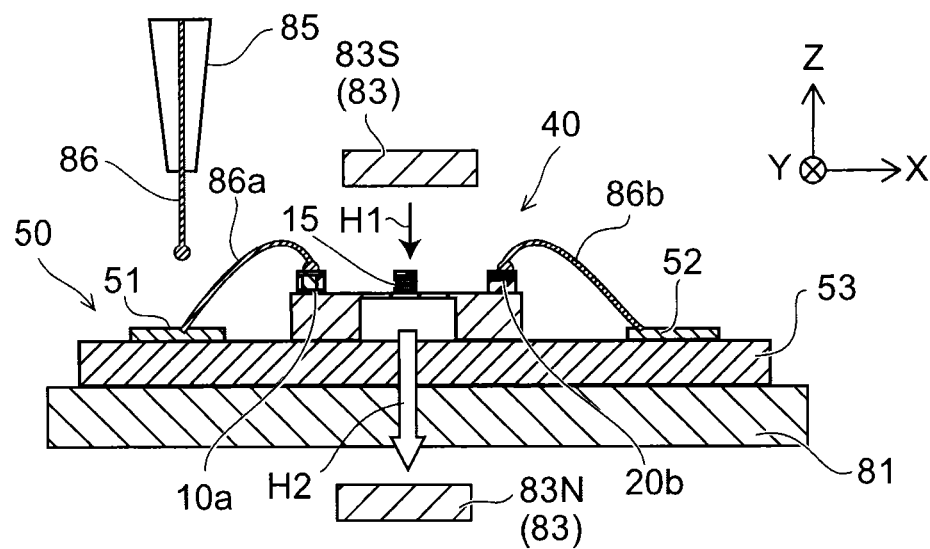

FIG. 11A and FIG. 11B are schematic cross-sectional views illustrating the process steps of still yet another method for manufacturing the pressure sensing device according to the first embodiment.

As shown in FIG. 11A, the sensor unit 40 is disposed on the first stage 81.

In this example, the magnetization direction H1 of the first magnetic layer 11 is along the Z-axis direction. The external magnetic field H2 applied by the magnetic field applying unit 83 is along the Z-axis direction (namely, the magnetization direction H1 of the first magnetic layer 11).

As shown in FIG. 11B, joining is performed while applying the external magnetic field H2 to the sensor unit 40. Also in the joining, heat and stress are applied to the first magnetic layer 11 when heating and joining the first interconnecting layer material 86a and the second interconnecting layer material 86b. In applying heat and stress, a change in the magnetization direction of the first magnetic layer 11 from the initial direction can be suppressed by applying the external magnetic field H2.

Second Embodiment

Figure 12:
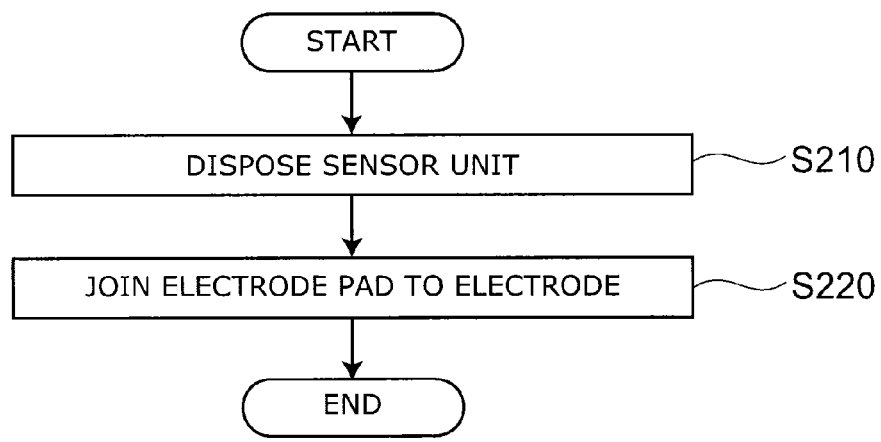
FIG. 12 is a flowchart illustrating a method for manufacturing a pressure sensing device according to a second embodiment.

FIG. 12 is a flowchart illustrating a method for manufacturing a pressure sensing device according to a second embodiment.

Figure 13:
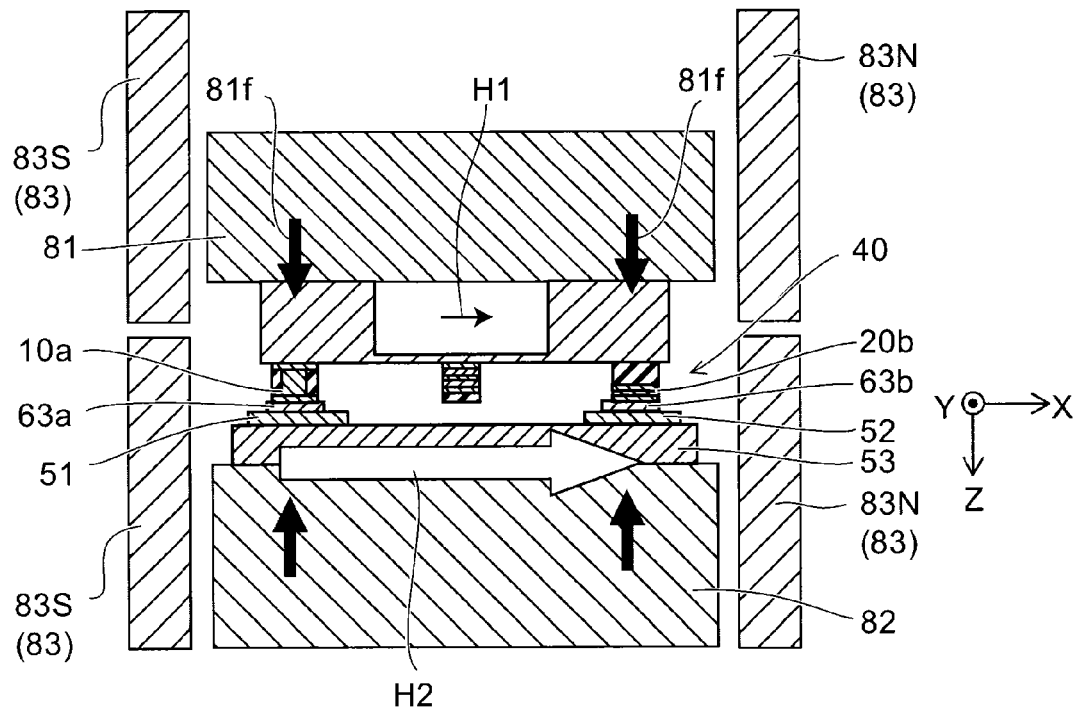
FIG. 13 is a schematic cross-sectional view illustrating a method for manufacturing the pressure sensing device according to the second embodiment.

FIG. 13 is a schematic cross-sectional view illustrating the method for manufacturing the pressure sensing device according to the second embodiment.

As shown in FIG. 12 and FIG. 13, in the method for manufacturing the pressure sensing device according to the embodiment, a sensor unit 40 is disposed on a stage (a first stage 81, for example) (Step S210). An electrode pad is joined to an electrode (Step S220). Since the configuration of the sensor unit 40 and the process step of a mounting substrate 50 are the same as the description made in the first embodiment, the description is omitted As shown in FIG. 13, in Step S220, joining is performed while applying an external magnetic field H2 along a magnetization direction H1 of a first magnetic layer 11 (along the X-axis direction in this example) to the sensor unit 40. In the joining, a first conductive adhesive layer 63a is inserted between a first electrode pad 51 of the mounting substrate 50 and a first portion 10a of the sensor unit 40, a pressure is applied across the first electrode pad 51 and the first portion 10a while heated, and the first electrode pad 51 is joined to the first portion through the first conductive adhesive layer 63a. A second conductive adhesive layer 63b is then inserted between a second electrode pad 52 and a fourth portion 20b, a pressure is applied across the second electrode pad 52 and the fourth portion 20b while heated, and the second electrode pad 52 is joined to the fourth portion 20b through the first conductive adhesive layer 63b.

For example, when the sensor unit 40 is disposed on the first stage 81, the sensor unit 40 is sometimes disposed in the state in which the sensor unit 40 is not substantially deformed. Also in this disposition, when a pressure is applied for joining using the conductive adhesive layers while heated, for example, stress is applied to the first magnetic layer 11, and strain occurs. In the joining, a change in the magnetization direction of the first magnetic layer 11 from the initial state can be suppressed by applying the external magnetic field H2.

Figure 14:
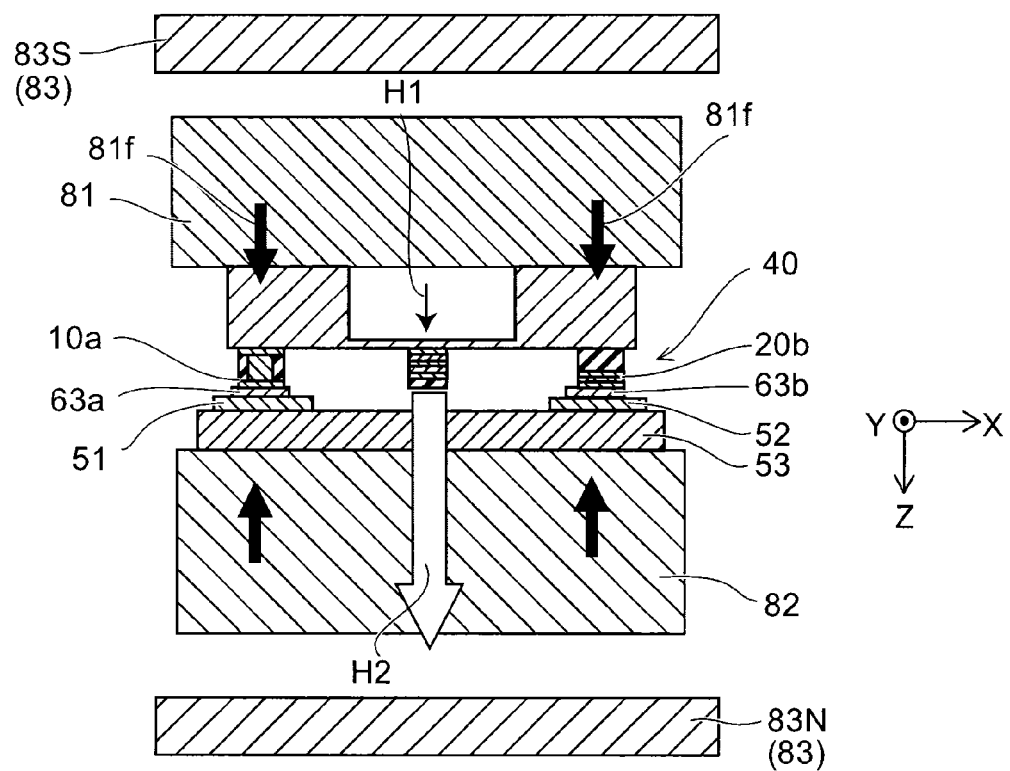
FIG. 14 is a schematic cross-sectional view illustrating another method for manufacturing the pressure sensing device according to the second embodiment.

FIG. 14 is a schematic cross-sectional view illustrating another method for manufacturing the pressure sensing device according to the second embodiment.

As shown in FIG. 14, in this example, the magnetization direction H1 of the first magnetic layer 11 applied to the sensor unit 40 is along the Z-axis direction. Joining is performed while applying the external magnetic field H2 along the Z-axis direction. Also in the joining, a pressure is applied while heated, the first electrode pad 51 is joined to the first portion through the first conductive adhesive layer 63a, a pressure is applied while heated, and the second electrode pad 52 is joined to the fourth portion 20b through the first conductive adhesive layer 63b, so that a change in the magnetization direction of the first magnetic layer 11 from the initial state can be suppressed by applying the external magnetic field H2.

In the following, an exemplary configuration of the sensor unit 40 according to the embodiment will be described.

The sensor unit 40 includes a spin valve film made of a stacked film of ultrathin magnetic films, for example. The resistance of the spin valve film is changed by an external magnetic field. The change value of the resistance is an MR change rate. The MR phenomenon is caused by various physical effects. The MR phenomenon is based on a giant magnetoresistive effect (GMR effect), or a tunneling magnetoresistive effect (TMR effect), for example.

The spin valve film has a configuration in which at least two ferromagnetic layers are stacked through a spacer layer. The magnetic reluctance state of the spin valve film is determined by a relative angle between the magnetization directions of two ferromagnetic layers. For example, when the magnetizations of two ferromagnetic layers are parallel with each other, the resistance of the spin valve film is low. When the magnetizations of two ferromagnetic layers are antiparallel, the parallelism of the spin valve film is high. In the case where an angle between the magnetizations of two ferromagnetic layers is an intermediate angle, an intermediate resistance state is obtained.

In at least two magnetic layers, a magnetic layer that magnetization tends to be easily rotated is a magnetization free layer, for example. A magnetic layer that magnetization does not tend to be relatively changed is a reference layer.

An external stress also changes the magnetization direction of the magnetic layer. The spin valve film can be used for a strain sensing device or a pressure sensing device using this phenomenon. A change in the magnetization of the magnetization free layer caused by strain is based on the inverse magnetostrictive effect, for example.

The magnetostrictive effect is a phenomenon that the strain of the magnetic material is changed when the magnetization of the magnetic material is changed. The magnitude of the strain is changed depending on the magnitude and direction of magnetization. The magnitude of the strain can be controlled through the parameters of the magnitude and direction of magnetization. A magnetostriction constant $\lambda s$ is the change value of strain where a strain value is saturated when the strength of a magnetic field to be applied is increased. The magnetostriction constant depends on characteristics unique to a magnetic material. The magnetostriction constant $(\lambda s)$ expresses the magnitude of a change in the shape where an external magnetic field is applied to saturate and magnetize a magnetic layer in a certain direction. Suppose that the value of strain is changed by $\Delta L$ when the external magnetic field is applied where a length is L with no external magnetic field, the magnetostriction constant $\lambda s$ is expressed by $\Delta L/L$. Although the change value is varied depending on the magnitude of an external magnetic field, the magnetostriction constant $\lambda s$ is expressed by $\Delta L/L$ in the state in which a sufficient external magnetic field is applied and magnetization is saturated. In the embodiment, preferably, the absolute value of the magnetostriction constant $\lambda s$ is $10^{-5}$ or more. Therefore, stress efficiently causes strain, and pressure sensing sensitivity is enhanced. The absolute value of the magnetostriction constant is $10^{-2}$ or less, for example. This value is the upper limit value of a practical material to cause the magnetostrictive effect.

There is an inverse magnetostrictive effect as an inverse phenomenon of the magnetostrictive effect. When an external stress is applied in the inverse magnetostrictive effect, the magnetization of a magnetic material is changed. The magnitude of the change depends on the magnitude of an external stress and the magnetostriction constant of a magnetic material. Since the magnetostrictive effect and the inverse magnetostrictive effect are physically symmetric effects to each other, the magnetostriction constant of the inverse magnetostrictive effect is the same as the magnetostriction constant of the magnetostrictive effect.

In the magnetostrictive effect and the inverse magnetostrictive effect, there are a positive magnetostriction constant and a negative magnetostriction constant. These constants depend on a magnetic material. In the case of a material having a positive magnetostriction constant, magnetization is changed along a direction to which tensile strain is applied. In the case of a material having a negative magnetostriction constant, magnetization is changed along a direction to which compressive strain is applied.

The magnetization direction of the magnetization free layer of the spin valve film can be changed by the inverse magnetostrictive effect. Since the inverse magnetostrictive effect changes the magnetization direction of the magnetization free layer when applying an external stress, a difference occurs in a relative magnetization angle between the reference layer and the magnetization free layer. This difference changes the resistance of the spin valve film, so that the spin valve film can be used for a strain sensing device.

The strain sensing device is formed on "a membrane", for example. The membrane serves like an eardrum that converts pressure into strain. A strain sensing device formed on the membrane can read strain and detect pressure. A single crystal Si substrate is used for the membrane, for example. Etching is performed from the back surface of a single crystal Si substrate to reduce the thickness of a portion, on which the strain sensing device is disposed, for forming a diaphragm. The diaphragm is deformed according to a pressure to be applied.

For example, in the case where the shape of a first major surface 30a of the diaphragm (a membrane body 30, for example) when projected onto the X-Y plane is a geometrically isotropic shape, strain caused by diaphragm displacement has the same value on the X-Y plane near the geometrical center point. Therefore, when the strain sensing device is disposed on the geometrical center point of the diaphragm, strain that rotates magnetization becomes isotropic, so that the magnetization of the magnetic layer is not rotated, and the resistance of the device is not changed. For this reason, in the embodiment, preferably, the strain sensing device is not disposed at the geometrical center point of the diaphragm. For example, in the case where the shape of the diaphragm when projected onto the X-Y plane is a circular shape, diaphragm displacement causes the maximum anisotropy strain near the outer circumferential portion of the circular shape. For this reason, the sensitivity of the pressure sensing device is increased when the strain sensing device is disposed near the outer circumferential portion of the diaphragm.

In the embodiment, Si can be used for the membrane, for example. Alternatively, the membrane is a flexible substrate using a flexible material. A polymer material or the like is used for a flexible substrate, for example. For a polymer material, at least one of acrylonitrile butadiene styrene, cycloolefin polymer, ethylene propylene, polyamide, polyamide-imide, polybenzyl imidazole, polyethylene terephthalate, polycarbonate, polyethylene, polyethylene ether ketone, polyetherimide, polyethylene imine, polyethylene naphthalene, polyester, polysulfone, polyethylene terephthalate, phenol formaldehyde, polyimide, polymethylmethacrylate, polymethylpentene, polyoxymethylene, polypropylene, m-phenyl ether, poly p-phenyl sulfide, p-amide, polystyrene, polysulfone, poly vinyl cloride, polytetrafluoro-ethene, perfluoro alkoxy, fluorinated ethylene propylene, polyethylene tetrafluoroethylene, polyethylene chlorotrifluoroethylene, polyvinylidene fluoride, melamine formaldehyde, the liquid crystalline polymer, and urea-formaldehyde can be used, for example.

FIG. 15A to FIG. 15D are schematic perspective views illustrating the configuration and characteristics of the pressure sensing device according to the embodiment.

Figures 15A, 15B:
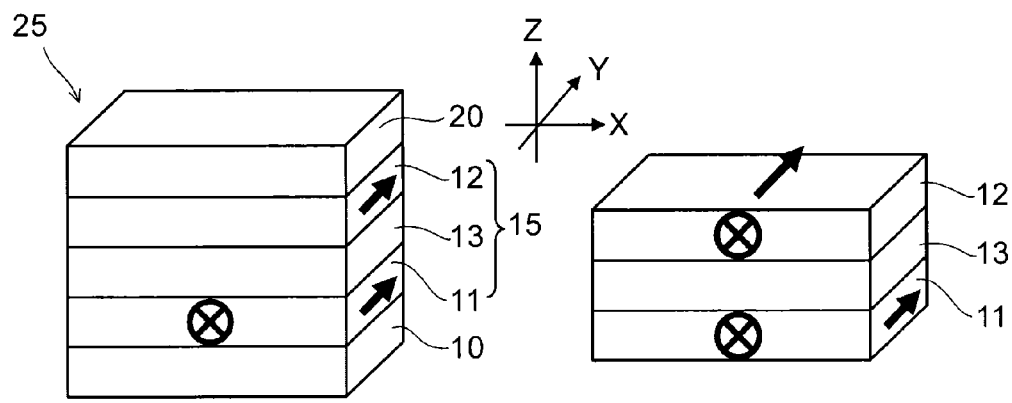
FIG. 15A to FIG. 15D are schematic perspective views illustrating a configuration and characteristics of the pressure sensing device according to the embodiment.
Figures 15C, 15D:
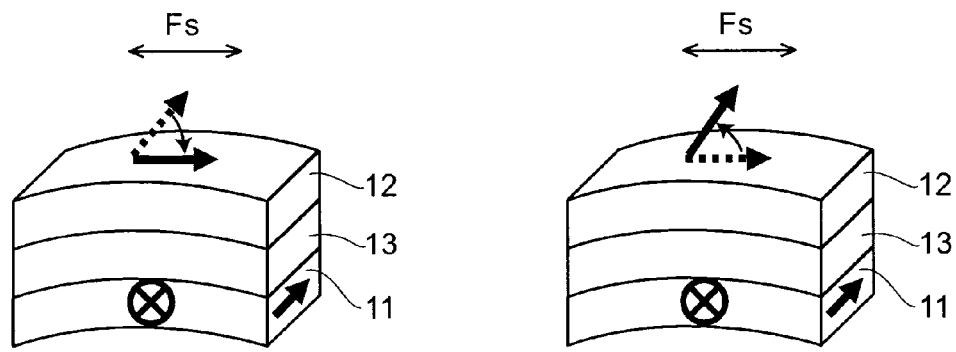

FIG. 15A illustrates the configuration of an element unit 25. FIG. 15B illustrates a strain sensing device 15 when stress is not applied. FIG. 15C illustrates the strain sensing device 15 when tensile stress is applied in the case where the strain sensing device 15 has a positive magnetostriction constant. FIG. 15D illustrates the strain sensing device 15 when tensile stress is applied in the case where the strain sensing device 15 has a negative magnetostriction constant.

As shown in FIG. 15A, the first magnetic layer 11 (a reference layer), the non-magnetic layer 13, the second magnetic layer 12 (a magnetization free layer), and the second electrode 20 are stacked on the first electrode 10 in this order. This example is an in-plane magnetization type. The magnetization direction of the first magnetic layer 11 (and the magnetization direction of the second magnetic layer 12) is substantially parallel with the X-Y plane, for example. The embodiment is not limited thereto. An angle between the magnetization direction of the first magnetic layer 11 and a direction parallel with the X-Y plane (the first major surface 30s) is smaller than an angle of 45 degrees. In the case where the magnetostriction constant of the magnetic layer is positive, the easy axis of the magnetic layer is parallel with the direction to which tensile stress is applied. In the case where the magnetostriction constant of the magnetic layer is negative, the easy axis of the magnetic layer is vertical to the direction to which tensile stress is applied.

As shown in FIG. 15B, when no stress is applied, the orientation of the magnetization of the second magnetic layer 12 (a magnetization free layer) is parallel with the orientation of the magnetization of the first magnetic layer 11 (a reference layer), for example. In this example, the orientation of magnetization is along the Y-axis direction.

As shown in FIG. 15C, for example, when a tensile stress Fs is applied along the X-axis direction, the magnetization of the second magnetic layer 12 is rotated to the X-axis direction by the inverse magnetostrictive effect of a positive magnetostriction constant. When the magnetization of the first magnetic layer 11 is fixed, a relative angle between the orientation of the magnetization of the second magnetic layer 12 and the orientation of the magnetization of the first magnetic layer 11 is changed. The electrical resistance of the strain sensing device 15 is changed according to a change in the relative angle.

As shown in FIG. 15D, for example, when the tensile stress Fs is applied along the Y-axis direction, the magnetization of the second magnetic layer 12 is rotated to the X-axis direction by the inverse magnetostrictive effect of a negative magnetostriction constant. Also in this case, the tensile stress Fs is applied to change a relative angle between the orientation of the magnetization of the second magnetic layer 12 and the orientation of the magnetization of the first magnetic layer 11. The electrical resistance of the strain sensing device 15 is changed according to a change in the relative angle.

FIG. 16A to FIG. 16D are schematic perspective views illustrating the configuration and characteristics of the pressure sensing device according to the embodiment.

Figures 16A, 16B:
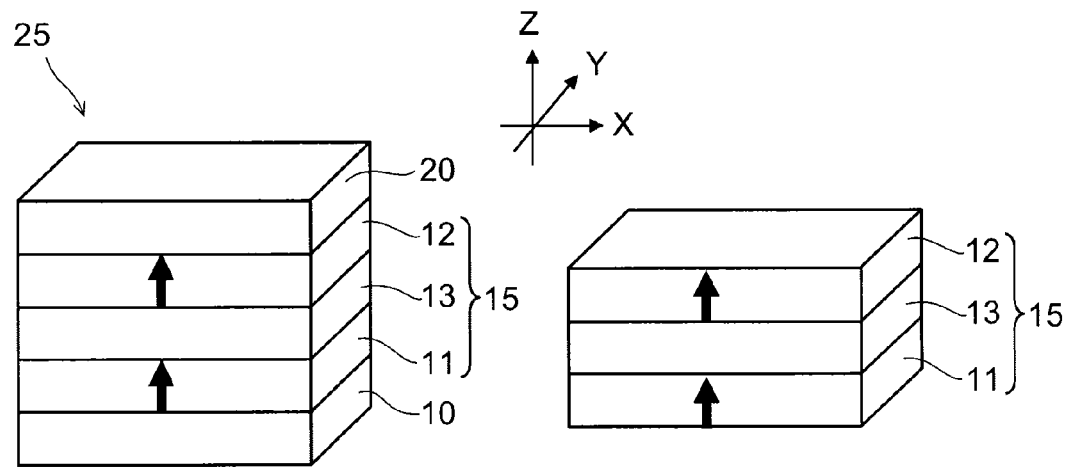
FIG. 16A to FIG. 16D are schematic perspective views illustrating a configuration and characteristics of the pressure sensing device according to the embodiment.
Figures 16C, 16D:
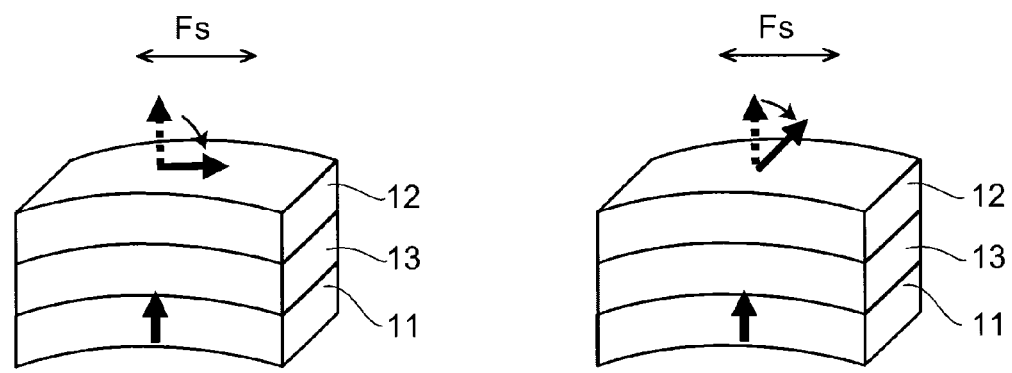

FIG. 16A illustrates the configuration of the element unit 25. FIG. 16B illustrates the strain sensing device 15 when stress is not applied. FIG. 16C illustrates the strain sensing device 15 when tensile stress is applied in the case where the strain sensing device 15 has a positive magnetostriction constant. FIG. 16D illustrates the strain sensing device 15 when tensile stress is applied in the case where the strain sensing device 15 has a negative magnetostriction constant.

As shown in FIG. 16A, this example is a perpendicular magnetization type. The magnetization direction of the first magnetic layer 11 (and the magnetization direction of the second magnetic layer 12) is substantially parallel with the Z-axis direction, for example. The embodiment is not limited thereto. An angle between the magnetization direction of the first magnetic layer 11 and a direction parallel with the X-Y plane (the first major surface 30s) is greater than an angle of 45 degrees.

As shown in FIG. 16B, when no stress is applied, the orientation of the magnetization of the second magnetic layer 12 (a magnetization free layer) is parallel with the orientation of the magnetization of the first magnetic layer 11 (a reference layer), for example. In this example, the orientation of magnetization is along the Y-axis direction.

As shown in FIG. 16C, for example, when the tensile stress Fs is applied along the X-axis direction, the magnetization of the second magnetic layer 12 is rotated to the X-axis direction by the inverse magnetostrictive effect of a positive magnetostriction constant. A relative angle between the orientation of the magnetization of the second magnetic layer 12 and the orientation of the magnetization of the first magnetic layer 11 is changed. The electrical resistance of the strain sensing device 15 is changed according to a change in the relative angle.

As shown in FIG. 16D, for example, when the tensile stress Fs is applied along the Y-axis direction, the magnetization of the second magnetic layer 12 is rotated to the X-axis direction by the inverse magnetostrictive effect of a negative magnetostriction constant. The tensile stress Fs is applied to change a relative angle between the orientation of the magnetization of the second magnetic layer 12 and the orientation of the magnetization of the first magnetic layer 11. The electrical resistance of the strain sensing device 15 is changed according to a change in the relative angle.

In the following, an exemplary configuration of the strain sensing device 15 will be described in the case of the in-plane magnetization type configuration.

For example, in the case where the first magnetic layer 11 is a reference layer, an FeCo alloy, a CoFeB alloy, an NiFe alloy, or the like can be used for the first magnetic layer 11, for example. The thickness of the first magnetic layer 11 is 2 nm (nanometers) or more and 6 nm or less, for example.

A metal or an insulator can be used for the non-magnetic layer 13. For a metal, Cu, Au, Ag, or the like can be used, for example. The thickness of the non-magnetic layer 13 in the case of using a metal is 1 nm or more and 7 nm or less, for example. For an insulator, magnesium oxide (such as MgO), aluminum oxide (such as $Al_2O_3$), titanium oxide (such as TiO), or zinc oxide (such as ZnO) can be used, for example. The thickness of the non-magnetic layer 13 in the case of using an insulator is 0.6 nm or more and 2.5 nm or less, for example.

In the case where the second magnetic layer 12 is a magnetization free layer, an FeCo alloy, an NiFe alloy, or the like can be used for the second magnetic layer 12, for example. In addition to this, an Fe—Co—Si—B alloy, a Tb-M-Fe alloy showing λs>100 ppm (where M is Sm, Eu, Gd, Dy, Ho, or Er), a Tb-M1-Fe-M2 alloy (where M1 is Sm, Eu, Gd, Dy, Ho, or Er, and M2 is Ti, Cr, Mn, Co, Cu, Nb, Mo, W, or Ta), an Fe-M3-M4-B alloy (where M3 is Ti, Cr, Mn, Co, Cu, Nb, Mo, W, or Ta, and M4 is Ce, Pr, Nd, Sm, Tb, Dy, or Er), Ni, Al—Fe, ferrite (such as $Fe_3O_4$ and $(FeCO)_3O_4$)), or the like can be used. The thickness of the second magnetic layer 12 is 2 nm or more, for example.

The second magnetic layer 12 can have a two layers structure. In this case, a stacked film of an FeCo alloy layer and the following layer is used. For a layer to be stacked on an FeCo alloy layer, a material selected from an Fe—Co—Si—B alloy, a Tb-M-Fe alloy showing λs>100 ppm (where M is Sm, Eu, Gd, Dy, Ho, or Er), a Tb-M1-Fe-M2 alloy (where M1 is Sm, Eu, Gd, Dy, Ho, or Er, and M2 is Ti, Cr, Mn, Co, Cu, Nb, Mo, W, or Ta), an Fe-M3-M4-B alloy (where M3 is Ti, Cr, Mn, Co, Cu, Nb, Mo, W, or Ta, and M4 is Ce, Pr, Nd, Sm, Tb, Dy, or Er), Ni, Al—Fe, ferrite (such as $Fe_3O_4$ and $(FeCo)_3O_4$)), and the like is used.

At least one of the magnetization directions of the first magnetic layer 11 and the second magnetic layer 12 is changed according to stress. The absolute value of the magnetostriction constant of at least one of the magnetic layers (that the magnetization direction is changed according to stress) is set to $10^{-5}$ or more, for example. With this setting, the inverse magnetostrictive effect sufficiently changes the magnetization direction according to an external strain.

For example, when an oxide such as MgO is used for the non-magnetic layer 13, a magnetic layer on the MgO layer generally has a positive magnetostriction constant. For example, in the case where the second magnetic layer 12 is formed on the non-magnetic layer 13, a magnetization free layer in a CoFeB/CoFe/NiFe stacked configuration is used for the second magnetic layer 12. When a topmost NiFe layer is a Ni-rich layer, the magnetostriction constant of NiFe is negative and the absolute value of NiFe is increased. In order to suppress the cancellation of a positive magnetostriction on the oxide layer, the Ni composition of the topmost NiFe layer is not made Ni-rich. More specifically, preferably, the Ni ratio of the topmost NiFe layer is less than 80 atom percent. In the case where the second magnetic layer 12 is a magnetization free layer, preferably, the thickness of the second magnetic layer 12 is 1 nm or more and 20 nm or less, for example.

In the case where the second magnetic layer 12 is a magnetization free layer, the first magnetic layer 11 may be a reference layer or a magnetization free layer. In the case where the first magnetic layer 11 is a reference layer, the magnetization direction of the first magnetic layer 11 is not substantially changed even though an external strain is applied. A relative magnetization angle between the magnetization direction of the first magnetic layer 11 and the magnetization direction of the second magnetic layer 12 changes the electrical resistance.

In the case where both of the first magnetic layer 11 and the second magnetic layer 12 are magnetization free layers, for example, the magnetostriction constant of the first magnetic layer 11 is different from the magnetostriction constant of the second magnetic layer 12.

In the case where the first magnetic layer 11 is a reference layer and in the case where the first magnetic layer 11 is a magnetization free layer, preferably, the thickness of the first magnetic layer 11 is 1 nm or more and 20 nm or less, for example.

In the case where the first magnetic layer 11 is a reference layer, a synthetic AF structure using a stacked structure of an antiferromagnetic layer/a magnetic layer/an Ru layer/a magnetic layer, for example, can be used for the first magnetic layer 11. IrMn or the like is used for the antiferromagnetic layer, for example. In the case where the first magnetic layer 11 is a reference layer, a configuration using a hard film is applied to the first magnetic layer 11, instead of using an antiferromagnetic layer. CoPt, FePt, or the like is used for a hard film, for example.

In the following, an exemplary configuration of the strain sensing device 15 will be described in the case of a perpendicular magnetization type configuration.

For example, in the case where the first magnetic layer 11 is a reference layer, a stacked configuration of CoFe (2 nm)/CoFeB (1 nm) can be used for the first magnetic layer 11, for example. A pinning layer fixes the magnetization direction to the membrane surface direction.

A metal or an insulator can be used for the non-magnetic layer 13. For a metal, Cu, Au, Ag, or the like can be used, for example. The thickness of the non-magnetic layer 13 in the case of using a metal is 1 nm or more and 7 nm or less, for example. For an insulator, magnesium oxide (such as MgO), aluminum oxide (such as $Al_2O_3$), titanium oxide (such as TiO), or zinc oxide (such as ZnO) can be used, for example. The thickness of the non-magnetic layer 13 in the case of using an insulator is 0.6 nm or more and 2.5 nm or less, for example.

In the case where the second magnetic layer 12 is a magnetization free layer, the second magnetic layer 12 has magnetization vertical to the membrane surface. In order to direct the magnetization direction vertical to the membrane surface, CoFeB (1 nm)/TbFe (3 nm), for example, can be used for the second magnetic layer 12, for example. CoFeB is used for the interface on MgO to improve the MR ratio. However, since a single CoFeB layer is difficult to form vertical magnetic anisotropy, an additional layer showing vertical magnetic anisotropy is used. For this function, a TbFe layer, for example, is used. When Tb is 20 atom percent or more and 40 atom percent or less, the TbFe layer shows vertical anisotropy. Such a stacked configuration is used to direct the magnetization direction of the entire magnetization free layer to the direction vertical to the membrane surface by the effect of the TbFe layer. The effect of the CoFeB layer in the MgO interface can maintain a large MR change rate. The TbFe layer has a significantly large positive magnetostriction constant, and the value is about $+10^{-4}$. This large magnetostriction constant easily implements a large magnetostriction constant of $+10^{-6}$ or more for the magnetostriction constant of the entire magnetization free layer. A magnetostriction constant greater than a magnetostriction constant of $+10^{-5}$ can be obtained as well.

In the case of the TbFe layer, it is possible to show two functions that the magnetization direction is directed vertically to the membrane surface and that a large magnetostriction constant is provided. An additional element may be added as necessary, while using this material.

In order to obtain vertical magnetic anisotropy, a material other than TbFe may be used. CoFeB (1 nm)/Co (1 nm)/Ni (1 nm))×n (where n is two or more) can be used for the second magnetic layer 12, for example. A (Co/Ni) multi-layer film shows vertical magnetic anisotropy. The thicknesses of a Co film and an Ni film are about 0.5 nm or more and 2 nm or less.

The absolute value of the magnetostriction constant of the entire magnetization free layer is $10^{-6}$ or more. In order to increase the magnetostriction constant, an additional layer such as FeSiB having a large magnetostriction constant is used. Since FeSiB shows a large positive magnetostriction constant (about $+10^{-4}$), a large positive magnetostriction constant can be obtained in the entire magnetization free layer. A configuration like CoFeB (1 nm)/Co (1 nm)/Ni (1 nm))×n/FeSiB (2 nm) can be applied, for example.

A stacked film of Mp and Ml can be applied to the second magnetic layer 12, for example. Mp is a magnetic layer showing vertical magnetic anisotropy, and Ml is a magnetic layer showing a large magnetostriction constant. For the second magnetic layer 12, a multi-layer film such as Mp/Ml, Ml/Mp, Mp/x/Ml, Ml/x/Mp, x/Ml/Mp, Ml/Mp/x, x/Mp/Ml, or Mp/Ml/x can be used. The additional layer x can be used as necessary, in the case where only Ml and Mp do not sufficiently provide functions. For example, in order to improve the MR change rate, a CoFeB layer, a layer CoFe, or the like can be used for the x layer provided in the interface between the second magnetic layer 12 and the non-magnetic layer 13.

For the magnetic layer Mp, CoPt—$SiO_2$ granular, FePt, CoPt, CoPt, a (Co/Pd) multi-layer film, a (Co/Pt) multi-layer film, or a (Co/Ir) multi-layer film can be used. The TbFe layer and the (Co/Ni) multi-layer film can be regarded as a material having an Mp function. The number of layers in the multi-layer film is two or more and ten or less, for example.

For the magnetic layer Ml, Ni, an Ni alloy (an alloy including a large amount of Ni such as $Ni_{95}Fe_5$), SmFe, DyFe, or a magnetic oxide material containing Co, Fe, or Ni can be used. The TbFe layer and the (Co/Ni) multi-layer film can be used for a layer that has a function of Mp as well as has a function of Ml. An amorphous alloy layer that FeSiB is a base can also be used. Ni, an Ni-rich alloy, and SmFe show a large negative magnetostriction constant. In this case, the sign of the magnetostriction of the entire magnetization free layer negatively functions. An oxide of a magnetic material containing Fe, Co, or Ni such as CoOx, FeO, or NiO ($0<x<0.8$) shows a large positive magnetostriction constant. In this case, the sign of the magnetostriction of the entire magnetization free layer is positive.

The Mp materials recited above can be used in order to show magnetic anisotropy vertical to the membrane surface. However, the CoFeB layer, which is considered to be the x layer used for the interface between the non-magnetic layer and the magnetic layer, can also function as Mp in some cases. In this case, the thickness of the CoFeB layer is reduced less than 1 nm to also show magnetic anisotropy vertical to the membrane surface.

In both of the cases of the in-plane magnetization type and the perpendicular magnetization type, Au, Cu, Ta, Al, or the like, which is a non-magnetic substance, can be used for the first electrode 10 and the second electrode 20, for example. A soft magnetic material can be used for the first electrode 10 and the second electrode 20. Accordingly, external magnetic noise that affects the strain sensing device 15 can be reduced. For a soft magnetic material, a permalloy (an NiFe alloy) or silicon steel (an FeSi alloy) can be used, for example.

The peripheral portion of the strain sensing device 15 is surrounded by the insulating layer 14. For the insulating layer 14, aluminum oxide ($Al_2O_3$, for example), silicon oxide ($SiO_2$, for example), or the like is used. The insulating layer 14 electrically insulates the first electrode 10 from the second electrode 20.

For example, in the case where the non-magnetic layer 13 is a metal, the GMR effect appears. In the case where the non-magnetic layer 13 is an insulator, the TMR effect appears. In the strain sensing device 15, the CPP (Current Perpendicular to Plane)-GMR effect, which a current passes along the stacking direction, is used, for example, According to the embodiment, a method for manufacturing a highly sensitive pressure sensing device can be provided.

As described above, the embodiments of the invention are described with reference to specific examples. However, the embodiments of the invention are not limited to these specific examples. For example, the specific configurations of the components such as the sensor unit, the electrode, the magnetic layer, the non-magnetic layer, the strain sensing device, the element unit, the membrane, the mounting substrate, the electrode pad, the conducting member, and the conductive adhesive layer included in the pressure sensing device and the specific configuration of the components such as stage and the magnetic field applying unit included in the fabrication apparatus are incorporated in the scope of the invention as long as a person skilled in the art appropriately selects components from the publicly known range to similarly implement the invention for obtaining the similar effect.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:

1. A method for manufacturing a pressure sensing device comprising:
    preparing a sensor unit and a mounting substrate,
        the sensor unit including:
            a membrane body; and
            an element unit provided on the membrane body,
                the element unit including:
                    a first electrode;
                    a second electrode; and
                    a first magnetic layer provided between the first electrode and the second electrode and having magnetization in a first direction;
        the mounting substrate including:
            a base;
            a first electrode pad provided on the base; and
            a second electrode pad provided on the base and provided apart from the first electrode pad; and
    joining the first electrode pad to the first electrode while heated, and joining the second electrode pad to the second electrode while heated, with an external magnetic field along the first direction applied to the sensor unit.

2. The method according to claim 1, wherein
    the first electrode has a first portion and a second portion;
    the second electrode has a third portion and a fourth portion; and
    the first magnetic layer is provided between the second portion and the third portion.

3. The method according to claim 2, wherein
    the sensor unit further includes:
        a second magnetic layer provided between the first magnetic layer and the third portion; and
        a non-magnetic layer provided between the first magnetic layer and the second magnetic layer,
        an angle between a magnetization direction of the first magnetic layer and a magnetization direction of the second magnetic layer is changed according to a strain of the membrane body.

4. The method according to claim 3, wherein
in the joining, joining the first electrode pad to the first portion, and joining the second electrode pad to the fourth portion.

5. The method according to claim 1, wherein the external magnetic field is greater than a saturation magnetic field of the first magnetic layer.

6. The method according to claim 5, wherein the saturation magnetic field is equal to or greater than 500 oersteds.

7. The method according to claim 1, wherein the external magnetic field is equal to or greater than an exchange coupling magnetic field of the first magnetic layer.

8. The method according to claim 7, wherein the exchange coupling magnetic field is equal to or greater than 3,000 oersteds.

9. The method according to claim 1, wherein the first magnetic layer is an in-plane magnetization film.

10. A method for manufacturing a pressure sensing device comprising:
preparing a sensor unit and a mounting substrate,
the sensor unit including:
a membrane body; and
an element unit provided on the membrane body,
the element unit including:
a first electrode having a first portion and a second portion;
a second electrode having a third portion and a fourth portion;
a first magnetic layer provided between the second portion and the third portion and having magnetization in a first direction;
a second magnetic layer provided between the first magnetic layer and the third portion; and
a non-magnetic layer provided between the first magnetic layer and the second magnetic layer,
an angle between a magnetization direction of the first magnetic layer and a magnetization direction of the second magnetic layer being changed according to a strain of the membrane body;
the mounting substrate including:
a base;
a first electrode pad provided on the base; and
a second electrode pad provided on the base and provided apart from the first electrode pad; and
joining the first electrode pad to the first portion while heated, and joining the second electrode pad to the fourth portion while heated, with an external magnetic field along the first direction applied to the sensor unit.

11. The method according to claim 10, wherein
joining the first electrode pad to the first portion includes inserting a first conductive adhesive layer between the first electrode pad and the first portion, applying a pressure across the first electrode pad and the first portion while heated, and joining the first electrode pad to the first portion, and
joining the second electrode pad to the fourth portion includes inserting a second conductive adhesive layer between the second electrode pad and the fourth portion, applying a pressure across the second electrode pad and the fourth portion while heated, and joining the second electrode pad to the fourth portion.

12. The method according to claim 10, wherein
joining the first electrode pad to the first portion includes inserting a first conducting member and a first thermoset resin layer provided around the first conducting member between the first electrode pad and the first portion, applying a pressure across the first electrode pad and the first portion while heated, and joining the first electrode pad to the first portion, and
joining the second electrode pad to the fourth portion includes inserting a second conducting member and a second thermoset resin layer provided around the second conducting member between the second electrode pad and the fourth portion, applying a pressure across the second electrode pad and the fourth portion while heated, and joining the second electrode pad to the fourth portion.

13. The method according to claim 10, wherein
joining the first electrode pad to the first portion includes joining a first interconnecting layer material to the first electrode pad while heated, and joining the first interconnecting layer material to the first portion while heated, and
joining the second electrode pad to the fourth portion includes joining a second interconnecting layer material to the second electrode pad while heated, and joining the second interconnecting layer material to the fourth portion while heated.

14. The method according to claim 10, wherein the external magnetic field is greater than a saturation magnetic field of the first magnetic layer.

15. The method according to claim 14, wherein the saturation magnetic field is equal to or greater than 500 oersteds.

16. The method according to claim 10, wherein the external magnetic field is equal to or greater than an exchange coupling magnetic field of the first magnetic layer.

17. The method according to claim 16, wherein the exchange coupling magnetic field is equal to or greater than 3,000 oersteds.

18. The method according to claim 10, wherein the first magnetic layer is an in-plane magnetization film.

19. The method according to claim 10, wherein the first magnetic layer is a perpendicular magnetization film.

20. The method according to claim 10, wherein the membrane body includes a polymer material.

* * * * *